US008265877B2

(12) United States Patent
Ramsay et al.

(10) Patent No.: US 8,265,877 B2
(45) Date of Patent: *Sep. 11, 2012

(54) APPARATUS AND METHOD FOR ANALYZING A METABOLITE PROFILE

(75) Inventors: Steven Lewis Ramsay, Igls (AT); Wolfgang Markus Stoeggl, Innsbruck (AT); Klaus Michael Weinberger, Mieming (AT); Armin Graber, Innsbruck (AT); Wolfgang Guggenbichler, Rum (AT)

(73) Assignee: Biocrates Life Sciences AG, Tirol (AT)

( * ) Notice: Subject to any disclaimer, the term of this patent is extended or adjusted under 35 U.S.C. 154(b) by 1244 days.

This patent is subject to a terminal disclaimer.

(21) Appl. No.: 11/476,637

(22) Filed: Jun. 29, 2006

(65) Prior Publication Data

US 2007/0004044 A1 Jan. 4, 2007

Related U.S. Application Data

(60) Provisional application No. 60/694,983, filed on Jun. 30, 2005, provisional application No. 60/694,984, filed on Jun. 30, 2005.

(51) Int. Cl.
G01N 33/48 (2006.01)
(52) U.S. Cl. ........................................... 702/19
(58) Field of Classification Search .................. 702/19
See application file for complete search history.

(56) References Cited

U.S. PATENT DOCUMENTS

| | | | |
|---|---|---|---|
| 6,258,605 B1 | 7/2001 | Chace | |
| 6,455,321 B1 | 9/2002 | Chace | |
| 6,627,444 B1 | 9/2003 | Goledzinowski et al. | |
| 2002/0009740 A1 | 1/2002 | Kaddurah-Daouk et al. | |
| 2003/0044799 A1 | 3/2003 | Matson | |
| 2003/0199102 A1 | 10/2003 | Ostrup | |
| 2004/0024543 A1 | 2/2004 | Zhang et al. | |
| 2005/0112635 A1 | 5/2005 | Gentle et al. | |
| 2006/0057554 A1 | 3/2006 | Watling et al. | |
| 2006/0228808 A1* | 10/2006 | Clarke et al. ................ | 436/173 |

FOREIGN PATENT DOCUMENTS

| | | |
|---|---|---|
| GB | 2 385 918 A | 9/2003 |
| JP | 2002-541459 A | 12/2002 |
| JP | 2004-503749 A | 2/2004 |
| JP | 2005-523448 A | 8/2005 |
| JP | 2007-516425 A | 6/2007 |
| JP | 2007-524844 A | 8/2007 |
| WO | WO 96/24062 A1 | 8/1996 |
| WO | WO 00/60361 A2 | 10/2000 |
| WO | WO 00/72019 A2 | 11/2000 |
| WO | WO 02/04957 A2 | 1/2002 |
| WO | WO-03/005628 | 1/2003 |
| WO | WO 03/016861 A2 | 2/2003 |
| WO | WO 03/089908 A1 | 10/2003 |
| WO | WO-2004/038381 A2 | 5/2004 |
| WO | WO-2004/038602 A1 | 5/2004 |
| WO | WO 2004/070523 A2 | 8/2004 |
| WO | WO 2004/101809 A2 | 11/2004 |
| WO | WO 2005/031304 A2 | 4/2005 |

OTHER PUBLICATIONS

Harrigan, G.G. & Goodacre, R. (2003) Metabolic profiling: Its role in biomarker discovery and gene function analysis. Kluwer Academic Publishers, Boston/Dordrecht/London. Chapters 1,4,8,9,10,11,13 and 17.
Schmidt, C. (2004) Journal of the National Cancer Institute, vol. 96, No. 10, pp. 732-734.
Raudys, S. (2001) Statistical and neural classifiers, Springer-Verlag, London. Contents, Chapters 1-6 and Appendices.
Daviss, B. (2005)The Scientist, vol. 19.,"Gowing Pains for Metabolomics", pp. 25-28.
Beecher C., (2003). In Harrigan, G.G., Goodacre, R.(Ed). Metabolic profiling: Its role in biomarker discovery and genge function analysis (pp. 311-319). Kluwer Academic Publishers, Boston/Dordecht/London.
Dunn, W.B. et al. (2005) Analyst, vol. 130, pp. 606-625.
Biomarkers Definitions Working Group. (2001) Clinical Pharmacology and Therapuetics, vol. 69, pp. 89-95.
Stoughton, R.B. & Friend, S.H. (2005) Nature Reviews. Drug Discovery, vol. 4, pp. 345-350.
Morris, M., & Watkins, S.M. (2005). Current Opinion in Chemical Biology., vol. 9, pp. 407-412.
McCandless, S.E. (2004). Primary Care, vol. 31, pp. 583-604.
Roschinger, W. et al. (2003). European Journal of Pediatrics, vol. 162 (Suppl 1), pp. S67-S76.
Strauss, A.W. (2004). J Clin Invest 2004: vol. 113, pp. 354-356.
Kaltashov, I.A. & Eyles, S.J. (2005) Mass spectrometry in biophysics: Conformation and dynamics of biomolecules. Wiley Contents, Chapters 1-11.
JPO Office Action, Appl. No. 2008-518726, Dec. 1, 2010, pp. 1-5 (w/ English translation). Altria, "Overview of Capillary Electrophoresis and Capillary Electrochromatography," Journal of Chromatography, 1999, vol. 856, pp. 443-463.
Bayerl et al, "Physical Properties of Single Phospholipid Bilayers Adsorbed to Micro Glass Beads," Biophysical Journal, 1990, vol. 58, pp. 357-362.
Examination Report dated Apr. 26, 2010 issued in corresponding Canadian Patent Application No. 2,608,965.
Flora et al, "High-Mass Accuracy of Product Ions Produced by SORI-CID Using a Dual Electrospray Ionization Source Coupled with FTICR Mass Spectrometry," Analytical Chemistry, 2001, vol. 73, No. 6, pp. 1247-1251.

(Continued)

Primary Examiner — Jerry Lin
(74) Attorney, Agent, or Firm — Birch Stewart Kolasch & Birch, LLP

(57) ABSTRACT

An apparatus and method analyzes a metabolic profile in a biological sample. The apparatus includes an input unit for inputting the drugs and/or metabolites to be screened; a controlling unit for determining a parameter set for metabolites preparation and for mass spectrometry analysis depending on the input of the kind of metabolites to be screened; a treatment unit for preparing the metabolites to be screened depending on the determined parameter set; a mass spectrometer for performing mass spectrometry analysis on prepared metabolites depending on the parameter set; a database for storing results of analyzing and parameter sets for metabolite preparation and for mass spectrometry analyses; and an evaluation unit for evaluating the results of mass spectrometry by use of reference results stored in the database to output an analysis of the metabolites profile.

12 Claims, 14 Drawing Sheets

OTHER PUBLICATIONS

International Search Report and Written Opinion of the International Searching Authority dated Feb. 2, 2007 for Application No. PCT/EP2006/006328 (PCT/ISA/220, PCT/ISA/210 and PCT/ISA/237).

Notice of Reasons for Rejection mailed Sep. 21, 2010 for Japanese Application No. 2008-518727.

Tanaka, Y. et al, "Microvolume Blood-Sampling Device with Low Hemolysis and High Consistent Yield of Serum Components," Clinical Chemistry, 2001, vol. 47, No. 10, pp. 1829-1835.

USPTO Notice of Allowance for U.S. Appl. No. 11/476,657 dated Oct. 28, 2011.

USPTO Office Action for U.S. Appl. No. 11/476,657 dated Jul. 20, 2011.

USPTO Office Action for U.S. Appl. No. 11/476,657 dated Oct. 29, 2010.

* cited by examiner

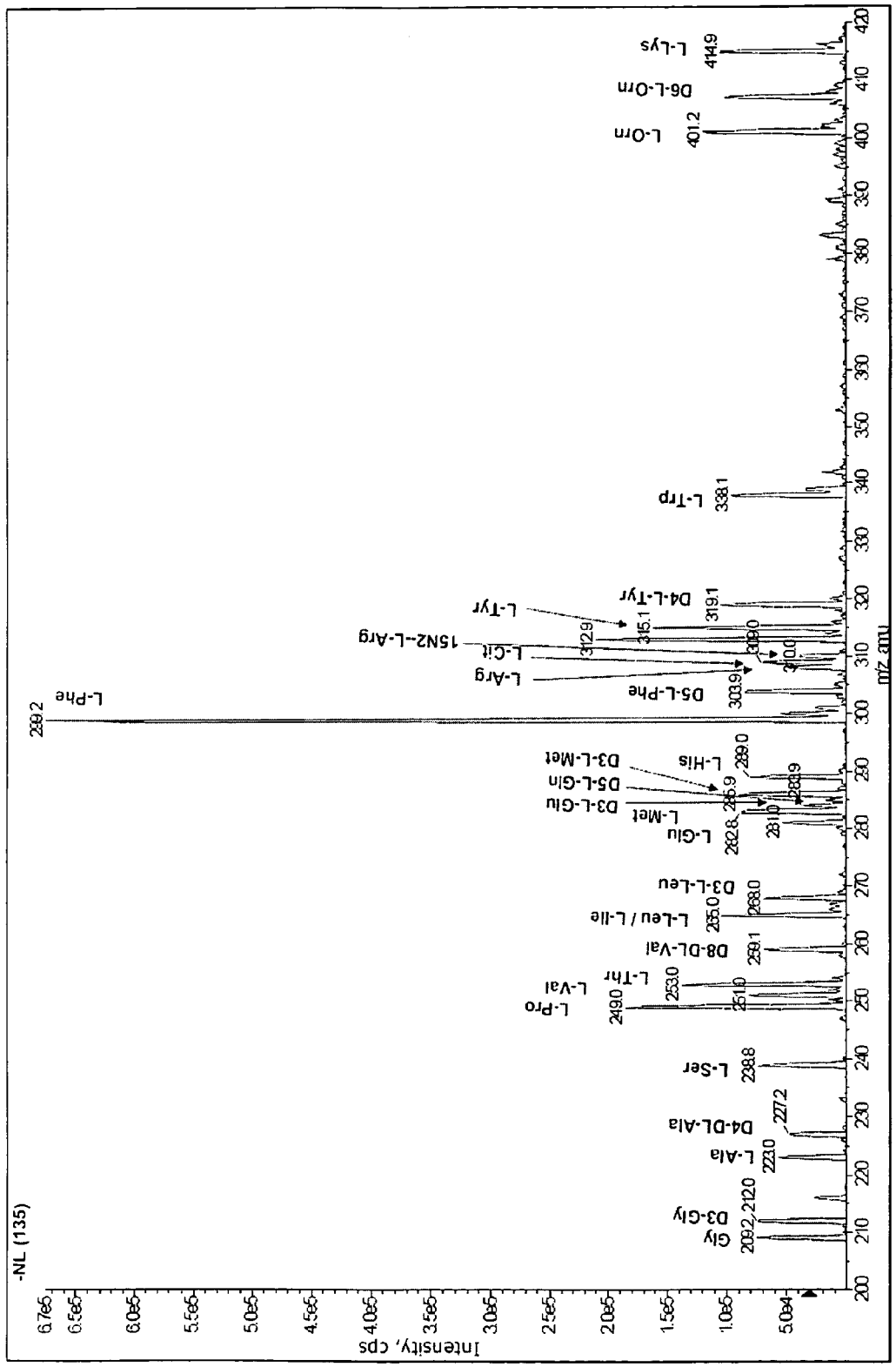
Figure 8. Phenylthiourea derivatives of a selection of amino acid standards and internal standards (stable isotopes)

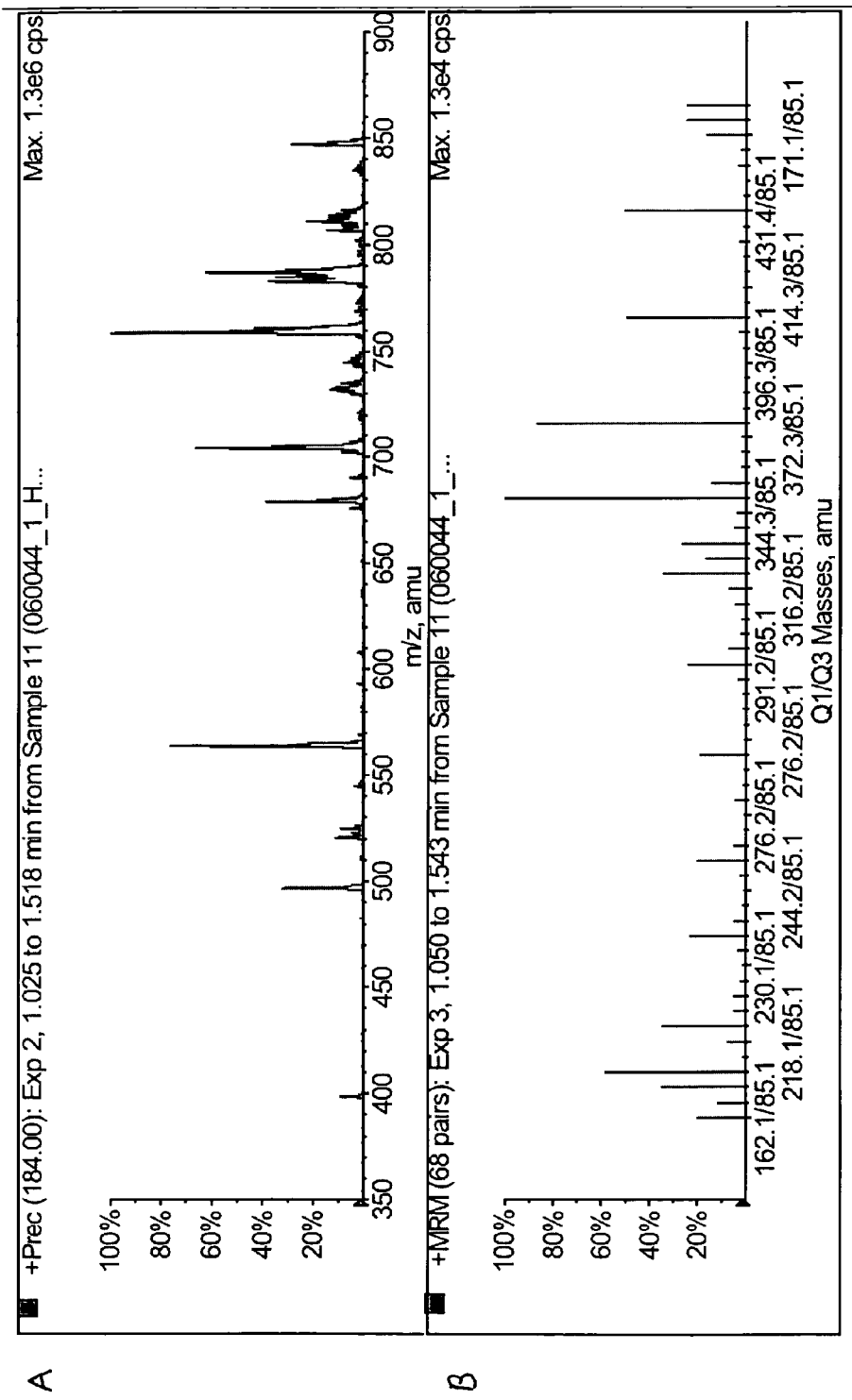
Figure 9. A shows precursor ion of 184 specific for choline-containing lipids like sphingomyelins and phosphatidylcholines and B; multiple reaction monitoring (MRMs) of individual acylcarnitines, all extracted from plasma

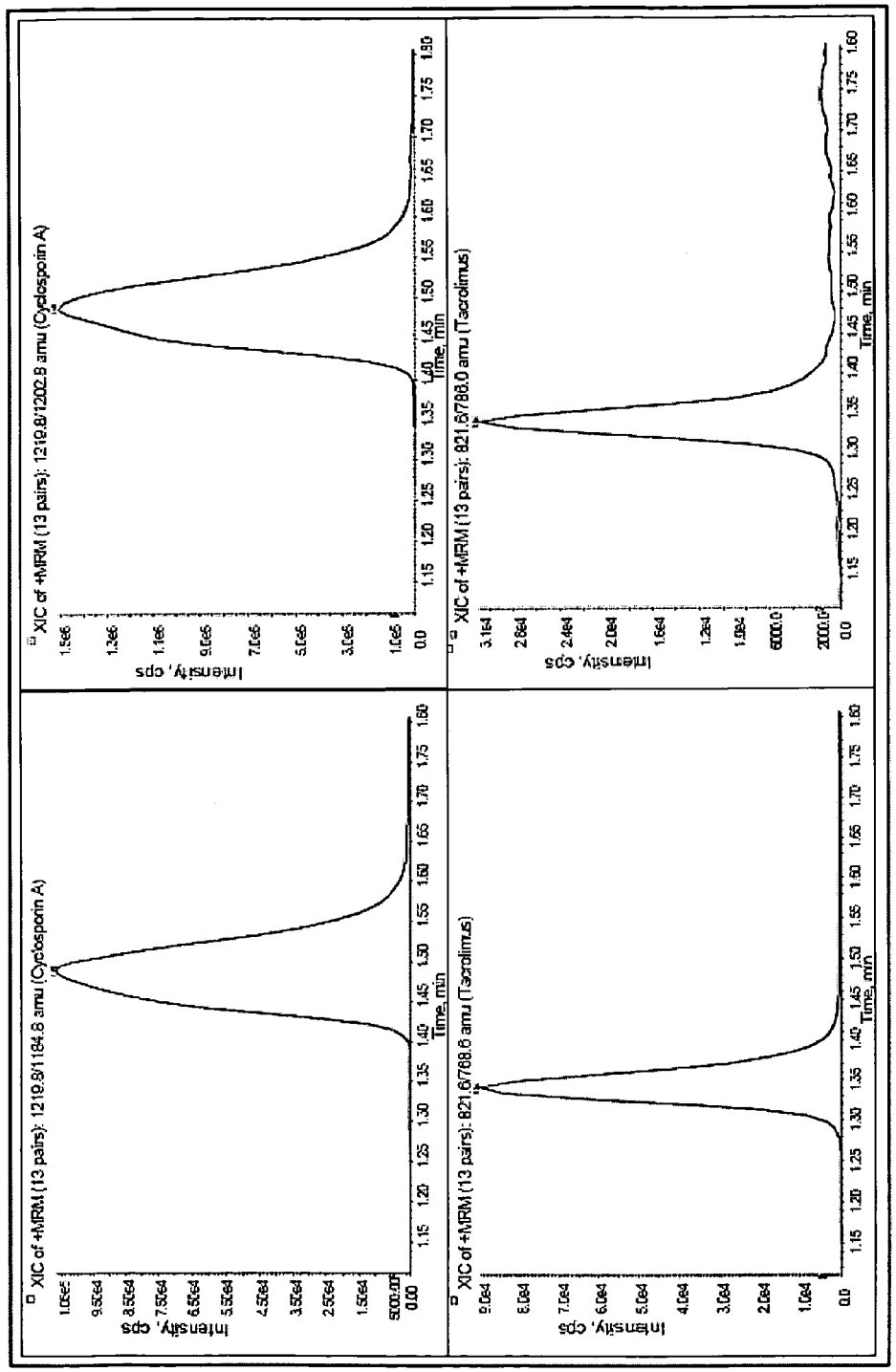
Figure 10a. Multiple MRM transitions of therapeutic drugs Cyclosporin A and Tacrolimus from a quality control blood sample

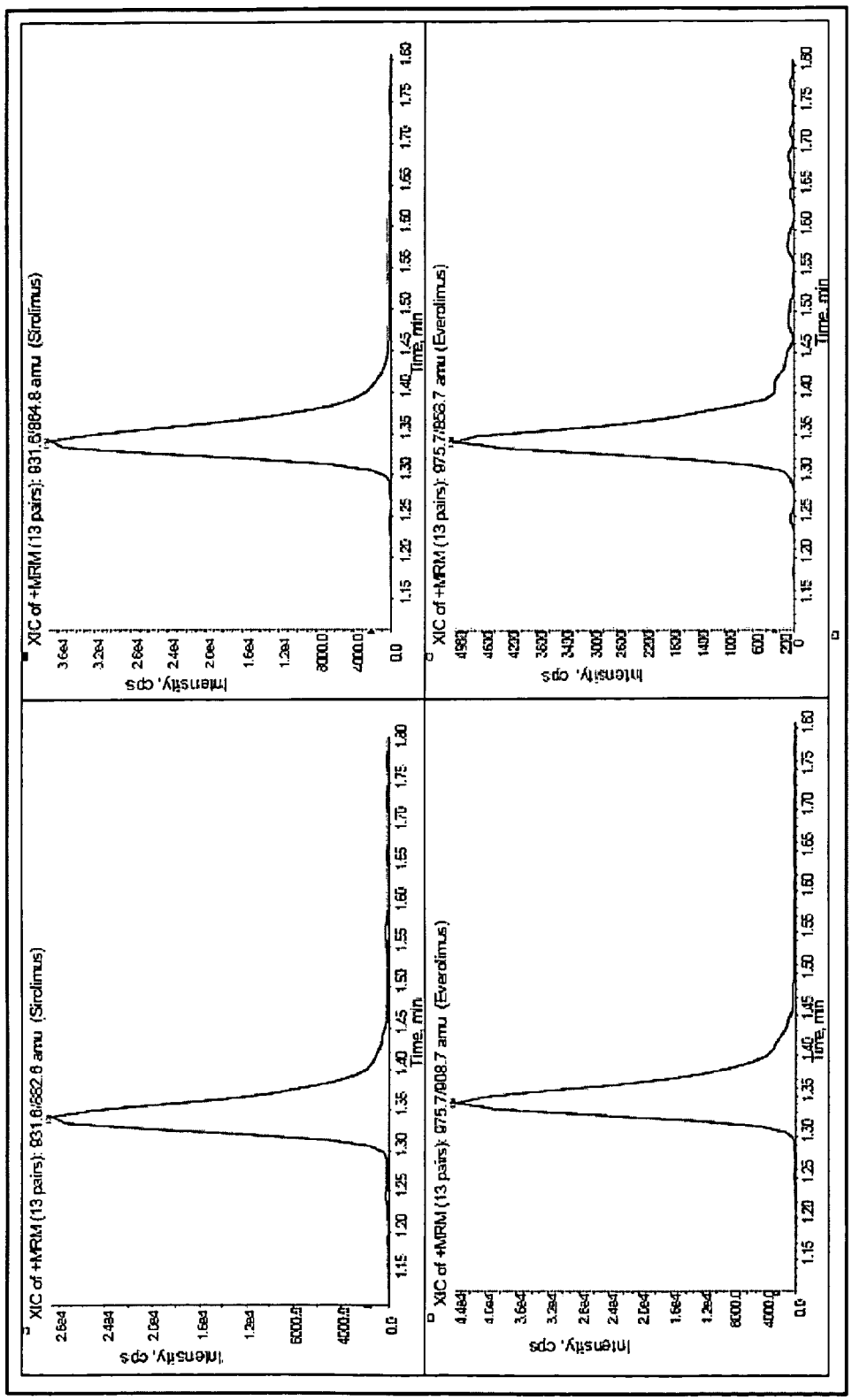
Figure 10b. Multiple MRM transitions of therapeutic drugs Sirolimus and Everolimus from a quality control blood sample

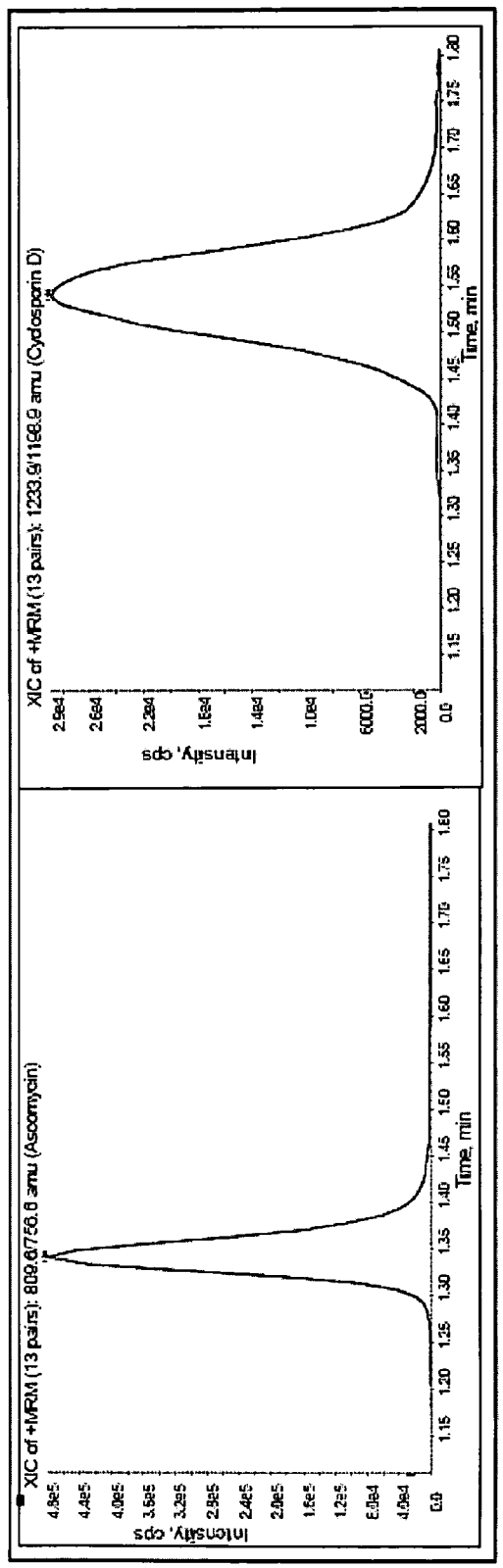
Figure 10c. Multiple MRM transitions of Internal standards Ascomycin and Cyclosporin D from a quality control blood sample

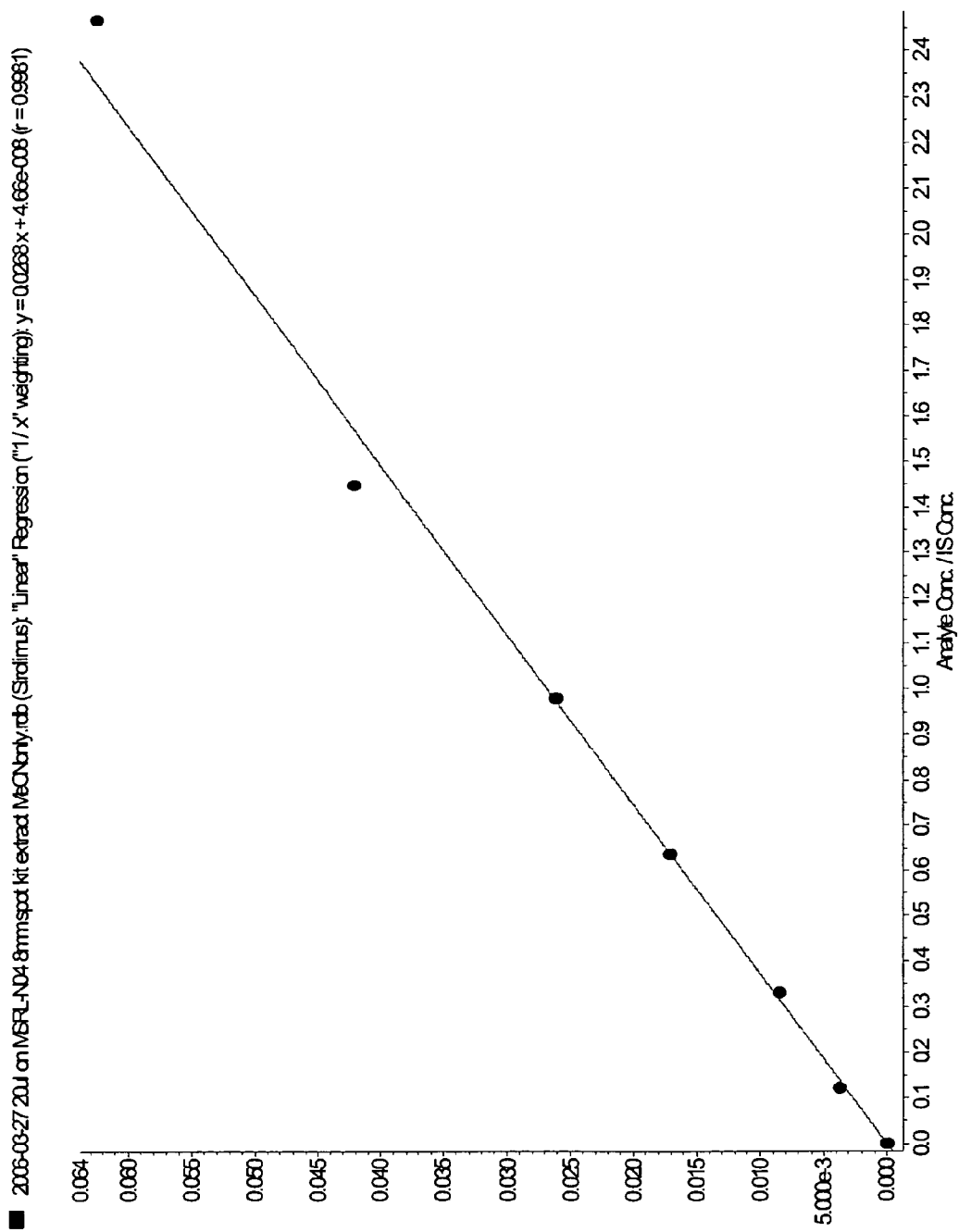
Figure 11. Sirolimus calibration curve (r=0.9981)

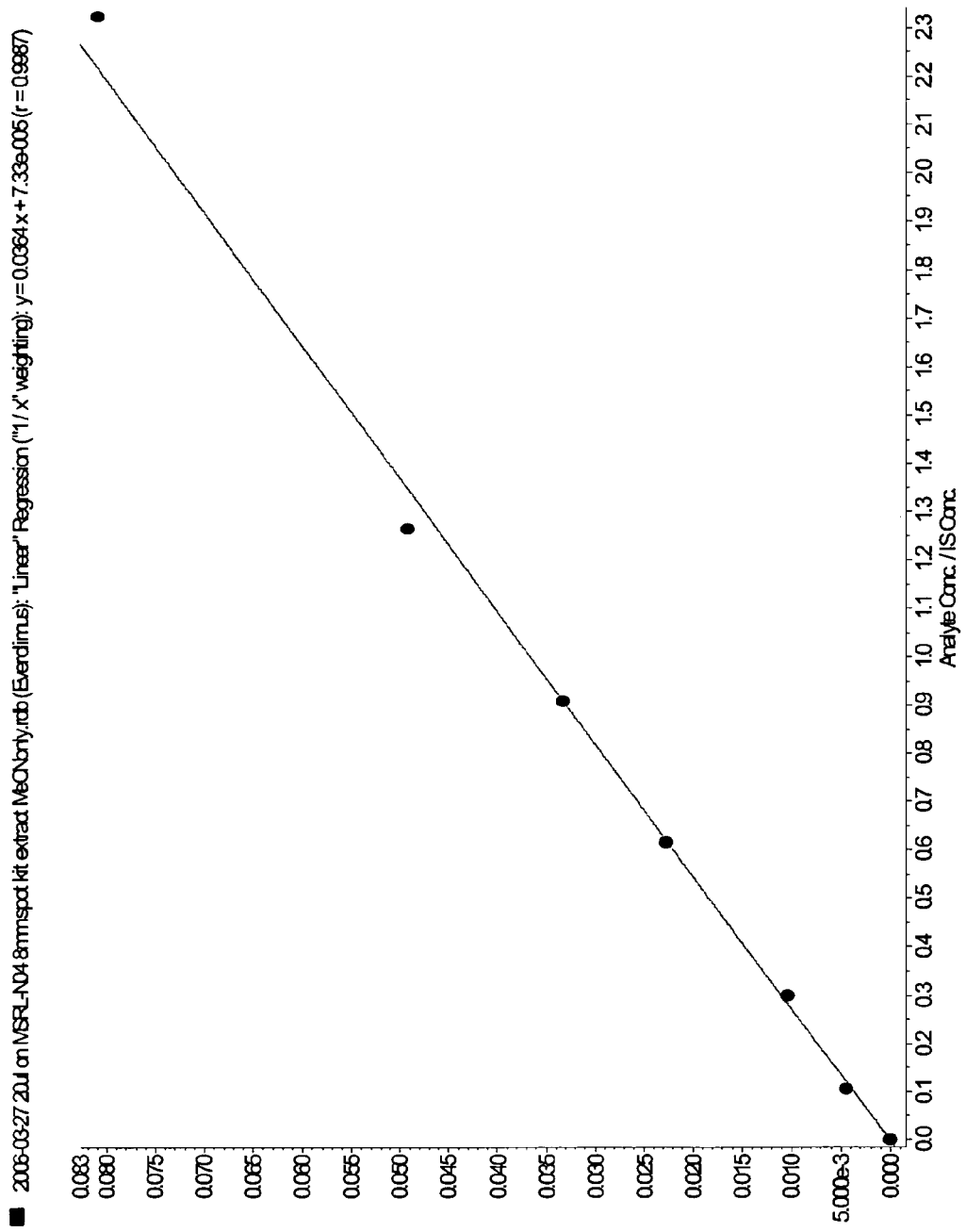
Figure 12. Everolimus calibration curve (r=0.9987)

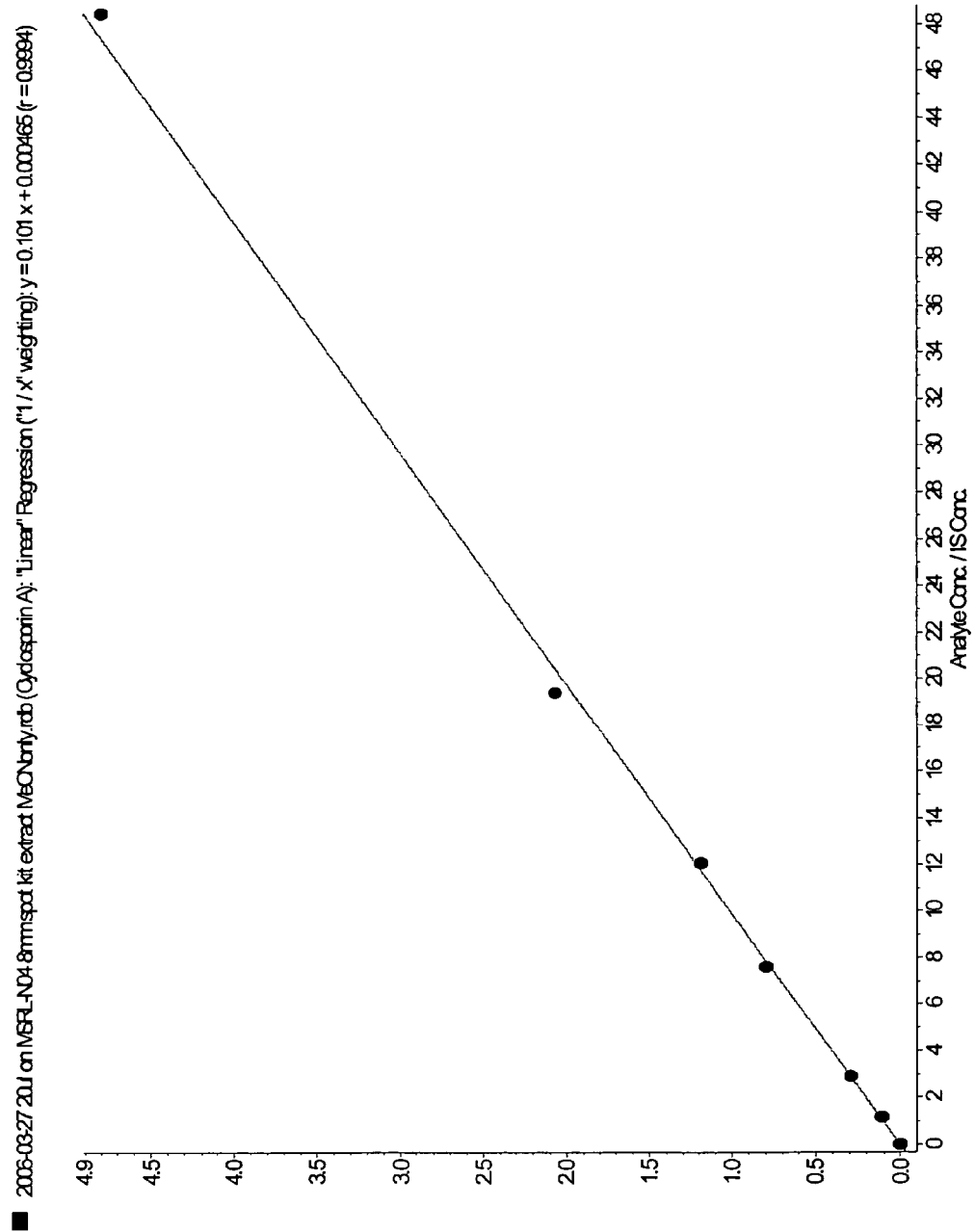
Figure 13. Cyclosporin A (Cyc A) calibration curve (r=0.9994)

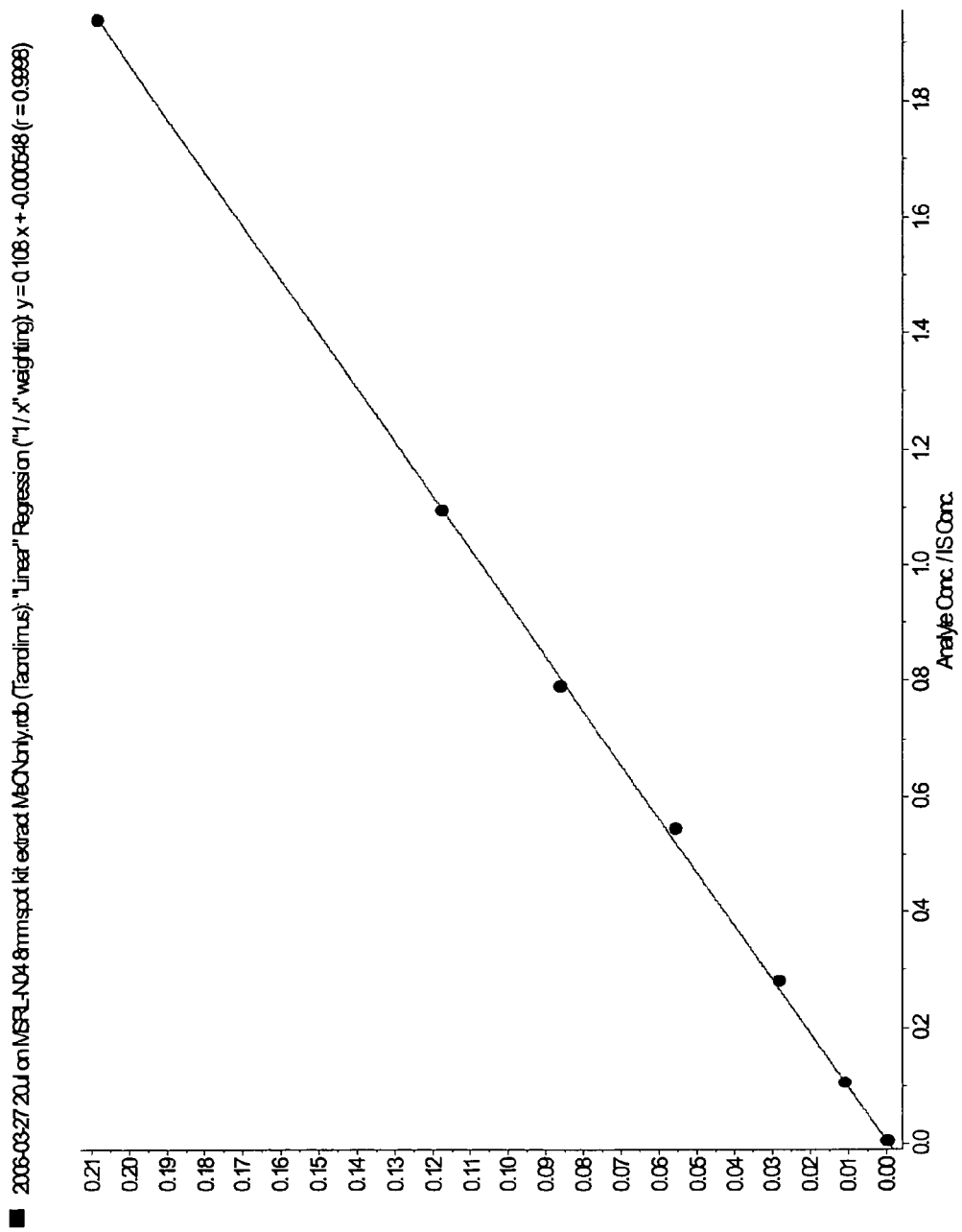
Figure 14. Tacrolimus calibration curve (r=0.9998)

APPARATUS AND METHOD FOR ANALYZING A METABOLITE PROFILE

This application claims priority of U.S. application Nos. 60/694,983 and 60/694,984, each filed Jun. 30, 2005, the entire contents of which are hereby incorpated by reference.

BACKGROUND OF THE INVENTION

1. Field of the Invention

The invention relates to an apparatus for analyzing a drug profile and/or a metabolite profile in a biological sample. The invention further relates to a method for analysis of a drug and/or a metabolite profile in a biological sample.

2. Description of the Related Art

Metabolomics is generally defined as the analysis of a substance or group of substances necessary for or taking part in a particular metabolic process in a human or animal body. It's also known as the metabolome analysis. Metabolomics is an evolving discipline that studies unique chemical fingerprints reflecting metabolic changes related to disease onset and progression. Metabolite profiling, an area within metabolomics, measures small molecules or metabolites, contained in a human cell, tissue or organ, which are involved in primary and intermediary metabolism. The biochemical information resulting from metabolite analysis reveals functional endpoints associated with physiological and pathophysiological processes, influenced by both genetic predisposition and environmental factors, such as nutrition, exercise or medication (Harrigan, G. G. & Goodacre, R. (2003) Metabolic profiling: Its role in biomarker discovery and gene function analysis. Kluwer Academic Publishers, Boston/Dordrecht/London; Schmidt, C. (2004), *Journal of the National Cancer Institute,* 96, 732-734; Raudys, S. (2001) *Statistical and neural classifiers,* Springer-Verlag, London; Daviss, B. (2005) *The Scientist,* 19, 25-28).

Metabolite profiling in combination with data mining approaches have the potential to revolutionize clinical diagnosis and drug development. In particular, big pharma companies are under continuous pressure to discover new targets and novel, more efficacious and safer compounds, and expedite biomarker and drug discovery, and generally lower costs of pharmaceutical development. Therefore they rely increasingly on biotech companies to fill this innovative gap and future pipelines. In this context, innovative bioanalytical and data mining techniques will play a fundamental role in saving costs by reducing time to market and drug attrition rates.

Recently, due to significant advances in high-throughput technologies, a wider set of the human metabolome—a thus far largely unexplored source of bioinformation—is now accessible (Beecher, C. (2003). In Harrigan, G. G., Goodacre, R. (Ed). *Metabolic profiling: Its role in biomarker discovery and gene function analysis* (pp. 311-319). Kluwer Academic Publishers, Boston/Dordrecht/London; Dunn, W. B., Bailey, N. J. & Johnson, H. E. (2005) *Analyst,* 130, 606-625). Statistical comparison of metabolite profiles can expose multivariate patterns that have the potential to revolutionize the health care system by specifically capturing latent warning signs of up-coming diseases before any disease symptoms show up. Early disease screening and prevention, opposed to late disease detection and expensive therapeutic interventions, is probably the primary solution to affordable health care coverage in the future. By definition, these so called biomarkers are "objectively measured indicators of normal biological processes, pathogenic processes or pharmacological responses to a therapeutic intervention, and intend to substitute for a clinical endpoint (predict benefit or harm) based on epidemiologic, therapeutic, pathophysiologic or other scientific evidence" (Biomarkers Definitions Working Group. (2001) *Clinical Pharmacology and Therapeutics,* 69, 89-95). Interest in the discovery of novel biomarkers originates from their broad range of potential applications and fundamental impact on pharmaceutical industry dynamics and current health care sector principles. Successful implementation of biomarkers in drug discovery can reduce the time and cost of drug development while the application to molecular diagnostics will improve patient compliance in clinical settings and reduce unnecessary costs resulting from false diagnosis in addition to late disease detection (Stoughton, R. B. & Friend, S. H. (2005) *Nature Reviews. Drug Discovery,* 4, 345-350); Morris, M., & Watkins, S. M. (2005) *Current Opinion in Chemical Biology,* 9, 407-412; McCandless, S. E. (2004) *Primary Care,* 31, 583-604).

Qualitative and quantitative metabolite profiling technologies include a range of advanced analytical and data processing tools, with the objective of utilizing potential markers as a result of comparison of small molecule components of biological systems. Tandem mass spectrometry (MS), for example, detects hundreds of metabolites simultaneously from micro liter quantities of biological samples, such as whole blood, serum, plasma, urine or other body fluids from minute amounts, with high precision and sensitivity (Roschinger, W., Olgemoller, B., Fingerhut, R., Liebl, B. & Roscher, A. A. (2003). *European Journal of Pediatrics,* 162 (Suppl 1), S67-76; Strauss, A. W. (2004). *J Clin Invest* 2004; 113:354-356; Kaltashov, I. A. & Eyles, S. J. (2005) *Mass spectrometry in biophysics: Conformation and dynamics of biomolecules,* Wiley). Quantification is achieved by reference to a wide range of appropriate internal standards. However, the amount of data or results which needs to interpreted is very voluminous.

For example, WO 03/005628 describes a method for generating, viewing, interpreting and analyzing a quantitative database of metabolites. Further, U.S. Publication 2002/0009740 describes methods for drug discovery, disease treatment and diagnosis using metabolomics. U.S. Pat. No. 6,455,321 describes a method for interpreting tandem mass spectrometry data for clinical diagnosis. U.S. Pat. No. 6,258,605 describes an analytical method to screen the newborn populations' acylcarnitine and amino acids from blood samples.

As a result, it is necessary to provide a method and an apparatus capable of identifying relevant information in biological samples to provide a drug and/or metabolite profile of a biological sample in a reliable way within a manageable time.

SUMMARY OF THE INVENTION

An object of the invention, in part, is to solve the aforesaid problems by an apparatus for analyzing a drug and/or metabolite profile in a biological sample containing at least one drug and/or metabolite.

The invention, in part, pertains to an apparatus that includes: an input unit for inputting the kind of drugs and/or metabolites to be screened, a controlling unit for determining a parameter set for sample preparation and for mass spectrometry analysis depending on the input of the kind of drugs and/or metabolites to be screened, a treatment unit for preparing the drugs and/or metabolites to be screened depending on the determined parameter set, a mass spectrometer for performing mass spectrometry analysis on prepared drugs and/or metabolites depending on the parameter set, a database for storing results of mass spectrometry analysis and/or parameter sets used for drug and/or metabolite preparation and for mass spectrometry analysis, an evaluation unit for evaluating and comparison of the results derived by mass spectrometry using reference results stored in the database, and for output of the analysis of the drug and/or metabolite profile included in the biological sample under consideration.

The invention, in part, relates in various regards to the idea, that by providing an apparatus for preparing a biological sample and for analyzing drugs and/or metabolites in a biological sample reproducible conditions for analyzing are kept over a wide range of analyses. Further, by providing an automated process for preparation of the biological sample and for mass spectrometry analysis, the comprehensive amount of data to be processed could be handled. By adapting the evaluation of the results of mass spectrometry utilizing reference results stored in the database, the analyses results derived from drug and/or metabolite profiles could be improved by use of the knowledge collected during previous analyses. Further, quantification by utilizing appropriate internal standards is used for quantifying the drugs and/or metabolites in a biological sample. By use of automated pre-analytical procedures, the amount of results is reduced. A plurality of standard operational procedures (SOP) is used for treating and handling a plurality of biological samples in a standardized way depending on the drugs and/or metabolites to be screened.

In the following, the invention is described with respect to the analysis of metabolite profiles. However, it should be understood that the invention is not restricted thereto but is also applicable to the analysis of drug profiles (i.e. for therapeutic drug monitoring, TDM) in a similar way.

One aspect of the invention, in part, provides for analysis of a metabolite profile in a biological sample that includes the following steps: providing the biological sample to an apparatus for analyzing at least one metabolite, providing information of the metabolites to be screened to the apparatus, preparing the biological sample depending on the information of metabolites to be screened, extracting the prepared metabolites, providing the mass spectrometer with the sample extract, performing one or more mass spectrometry analyses on the prepared metabolites, processing and evaluating results of mass spectrometry of the metabolites to be screened and compared with reference values and pre-annotated information of the targeted metabolites, and generating output data.

Thus, the method for analysis of a metabolite profile generally has main steps of sample preparation and separation of the metabolites, analysis by use of mass spectrometry and data processing.

There are two kinds of strategies which may be applied for metabolite profiling. When using mass spectrometry based metabolite profiling a qualitative non-targeted and the quantitative targeted approach can be used. Depending on the selected strategy the extent and type of subsequent data processing is determined.

A targeted profiling scheme may thus be used according to the invention to quantitatively screen for known small molecule metabolites using multiple reaction monitoring (MRM), precursor and neutral loss scans. A plurality of different classes of compounds (e.g. amino acids, peptides, acylcarnitines, monosaccharides, lipids, and phospholipids etc.) is selected for analyzing. These compounds cover relevant metabolic pathways of a disease being investigated. The quantification of the metabolites in the compounds of the biological sample is achieved by reference to appropriate internal standards.

The invention, in part, uses a known quantity of an internal standard, which is combined with the biological sample. By using the apparatus and the method for metabolite profiling the parts or aliquots of the biological sample to be screened are combined with a plurality of different internal standards. The internal standards are identified and quantified and, therefore, result in mass spectrometry data, which correspond to the known concentration. Further by dividing the biological sample into a plurality of aliquots only small amounts of biological sample are required. Each aliquot is treated and prepared in a standardized way, which is controlled by the use of the parameter set derived from the standard operation procedure (SOP). By using the automated sample preparation (treatment) and separation (e.g. derivatization, extraction), depending on the metabolites to be screened, it is possible to perform a mass spectrometry analysis on each extract of a respective aliquot, generating a mass spectrometry result having a plurality of peaks of the metabolites included in the prepared and separated aliquot and the peaks of the internal standards corresponding to know concentrations.

After mass spectrometry data processing is performed on the results of mass spectrometry analysis, data processing may use chemometric and statistical procedures including isotope correction, noise filtering, normalization and scaling, content based filtering of the results, and quantification and annotation of the targeted detected metabolites utilizing the known characteristics of the appropriate internal standards and the pre-annotated information in the database. The processed results may be stored and compared with reference values stored in the database to derive information whether the metabolites in the results belong, for instance, to a healthy or to diseased patient, or are characteristic for a certain disease stage, or reflect response to a pharmacological substance or drug. The database may be adapted based on information derived during comparing the results of the mass spectrometry with reference values stored in the database. This learning process may be used for providing an adaptation of the parameter sets and/or standard operational procedure, which are used for treating the biological samples for analysis of the metabolite profiles. The results of the method for analyzing metabolite profiles may be so called biomarkers, characterizing at least one or more very significant metabolites to indicate a disease or change of a normal healthy state of a patient, or response to pharmacological substance or drug.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

In the following, exemplary embodiments will be described by the accompanied drawings, in which:

FIG. 8 describes a neutral loss scan of 135 in negative mode using ion tandem mass spectrometry of phenylthiourea amino acid derivatives (PTU), showing amino acids from a red blood cell sample and their corresponding stable isotope internal standards prepared with the multi-device described in Example 2;

FIG. 9A describes a precursor scan 184 in positive ion mode (A), showing the multi-devices ability to extract phospholipids from a red blood cell sample of Example 2. For example sphingomyelins and phosphatidylcholines are observable in the m/z range 700-840, and lyso phosphatidylcholines in the m/z range 400-650;

FIG. 9B describes an MRM scan (multiple reaction monitoring) in positive ion mode of Example 2;

FIGS. 10A-10C describe examples of how immunotherapy drugs Sirolimus, Everolimus, Cyclosporin A, Tacrolimus, and internal standards Ascomycin and Cyclosporin D from a quality control blood sample are analyzed with LCMS to generate quantitative data. The area under the integrated peaks of the internal standard Cyclosporin D and Ascomycin, of known concentrations, are used for comparison against the area under the peak of the immunosuppressants in the five quality control samples containing known concentration amounts. This provides a measure of accuracy for all four drugs;

FIG. 11 describes a calibrator curve from calibrators for Sirolimus obtained from multi-device with cellulose insert (Example 3);

FIG. 12 describes a calibrator curve from calibrators for Everolimus obtained from multi-device with cellulose insert (Example 3);

FIG. 13 describes a calibrator curve from calibrators for Cyclosporin A obtained from multi-device with cellulose insert (Example 3); and FIG. 14 describes a calibrator curve from calibrators for Tacrolimus obtained from multi-device with cellulose insert (Example 3).

DETAILED DESCRIPTION

Figure 1:
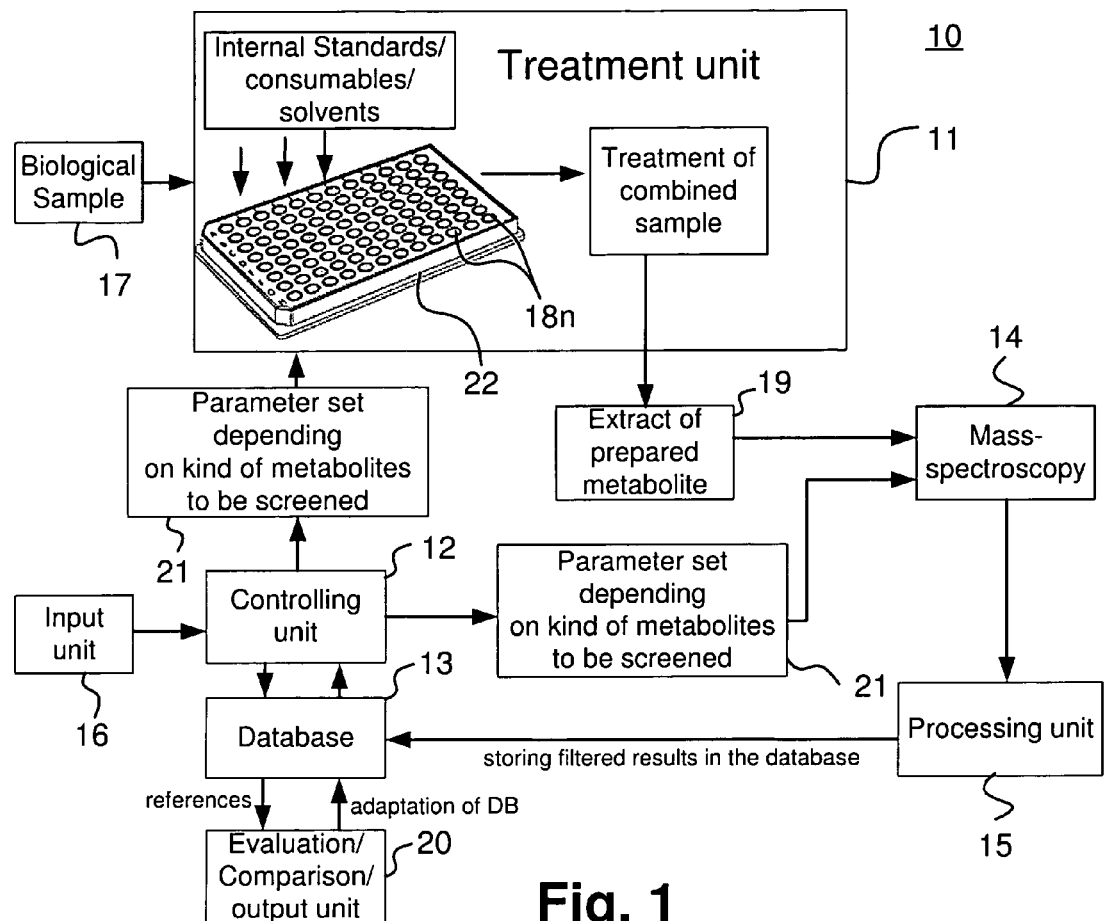
FIG. 1 shows a block diagram of an apparatus according to the invention.

Advantages of the invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Before explaining embodiments based on the figures some definitions or explanations are given.

Internal Standard

An internal standard as used in the invention should be understood to be any reference materials of known absolute amounts that are used for comparisons to similar or identical compounds in order to quantify unknown amounts of compounds present in a given sample. Preferably the internal standard is an organic internal standard. Internal standards as used in the invention may belong to the same group or family of compounds to be analyzed in the biological sample. However, they are preferably labelled with isotopes in order to properly allow a distinction between the metabolites of the sample and the internal standard. Any other way of distinguishing the metabolites of the sample from the internal standards, however, may also be used. For example, non-naturally occuring compounds may also be used as internal standards.

Specific examples for the internal standard as used in the invention are indicated in Table 1.

TABLE 1

| Lipids: | | |
|---|---|---|
| abbreviation | Full name | Comments Fatty acid chain length |
| SM(d18:1/6:0) | N-Hexanoyl-sphing-4-enine-1-phosphocholine | 6 |
| GPCho(9:0/0:0) | 1-Nonanoyl-sn-glycero-3-phosphocholine | 9 |
| GPCho(14:0/14:0) | 1,2-Ditetradecanoyl-sn-glycero-3-phosphocholine | 28 |
| GPIns(16:0/16:0) | 1,2-Dihexadecanoyl-sn-glycero-3-phospho-(1'-myoinositol) | 32 |
| GPCho(20:0/20:0) | 1,2-Di-(3,7,11,15 tetramethyl hexadecanoyl)-sn-glycero-3-phosphocholine | 40 |
| GPSer(20:0/20:0) | 1,2-Di-(3,7,11,15 tetramethyl hexadecanoyl)-sn-glycero-3-phosphoserine | 40 |
| GPSer(6:0/6:0) | 1,2-Dihexanoyl-sn-glycero-3-phosphoserine | 12 |

| Amino acids | | |
|---|---|---|
| Abbreviation | Full name | Comments |
| 13C2-15N-Gly | 13C2-15N-Glycine | |
| D4-DL-Ala | D4-DL-Alanine | |
| 15N2-L-Argl | 15N2-L-Arginine HCl | |
| D3-DL-Asp | D3-DL-Aspartic Acid | |
| 15N2-L-Asn | 15N2-L-Asparagine H2O | |
| D3-L-Glu | D3-L-Glutamic Acid | |
| D5-L-Gln | D5-L-Glutamine | |
| 13C6-L-His | 13C6-L-Histidine H2O | |
| 13C6-L-Ile | 13C6-L-Isoleucine | |
| 13C-L-Lys | 13C-L-Lysine 2HCl | |
| D3-L-Met | D3-L-Methionine | |
| D6-L-Orn | D6-L-Ornithine HCl | |
| D5-L-Phe | D5-L-Phenylalanine (ring 5-phe) | |
| D7-L-Pro | D7-L-Proline | |
| D3-DL-Se | D3-DL-Serine | |
| 13C4-L-Thr | 13C4-L-Threonine | |
| 15N2-L-Trp | 15N2-L-Tryptophan | |
| D4-L-Tyr | D4-L-Tyrosine (ring 4-tyr) | |
| D8-DL-Val | D8-DL-Valine | |

| Acylcarnitines | | |
|---|---|---|
| Abbreviation | Full name | side chain length |
| D3-C0 | [d3-methyl]-Carnitine.HCl | C = 0 |
| D9-C0 | [d9-trimethyl]-Carnitine.HCl | C = 0 |

TABLE 1-continued

| | | |
|---|---|---|
| D3-C2 | [d3]-Acetyl-L-carnitine.HCl | C = 2 |
| D3-C3 | [3,3,3-d3]-Propionyl-L-carnitine.HCl | C = 3 |
| D3-C4 | [4,4,4-d3]Butyryl-L-carnitine.HCl | C = 3 |
| D7-C4 | [d7]-Isobutyryl-L-carnitine.HCL | C = 4 |
| D3-C5 | [5,5,5,-d3]-Valeryl-L-carnitine.HCl | C = 4 |
| D9-C5 | [d9]-Isovaleryl-L-carnitine.HCl | C = 5 |
| D3-C6 | [6,6,6-d3]-Hexanoyl-L-carnitine.HCl | C = 6 |
| D3-C8 | [8,8,8-d3]-Octanoyl-L-carnitine.HCl | C = 8 |
| D3-C10 | [10,10,10-d3]-Decanoyl-L-carnitine.HCl | C = 10 |
| D3-C12 | [12,12,12-d3]-Dodecanoyl-L-carnitine.HCl | C = 12 |
| D3-C14 | [14,14,14-d3]-Tetradecanoyl-L-carnitine.HCl | C = 14 |
| D3-C16 | [16,16,16-d3]-Hexadecanoyl-L-carnitine.HCl | C = 16 |
| D3-C18 | [18,18,18-d3]-Octadecanoyl-L-carnitine.HCl | C = 18 |

Reducing monosaccharides

| Abbreviation | Full name | Comments |
|---|---|---|
| 13C6-Glc | 13C6-Glucose | |

Pyruvate/Lactate

| Abbreviation | Full name | Comments |
|---|---|---|
| 13C3-Pyr | 13C3-Pyruvate | |

Creatinine

| Abbreviation | Full name | Comments |
|---|---|---|
| | [d3-methyl]-Creatinine | |

Immunosuppressants

| Abbreviation | Full name(s) | Comments |
|---|---|---|
| | Ascomycin | |
| | Cyclosporin D | |
| | 32-Desmethoxyrapamycin | |

Biological Sample

A biological sample as used in the invention should be understood to be any sample of, relating to, caused by, or affecting life or living organisms, biological processes, such as growth and digestion.

Examples of a biological sample may include, but are not limited to blood, cell culture supernatant, saliva, tears, urine, blood, serum, plasma, sweat, vaginal fluids, semen, feces, mucous, breast milk, ascites, lymph, pleural effusion, synovial fluid, bone marrow, cerebro-spinal fluid, and washings from bodily cavities (e.g., bronchial lavage), hair, tissue, bones, or teeth.

Preferably, the biological sample is a liquid sample. More preferably, the biological sample is blood, and most preferable human blood. Liquid means a state of matter with definite volume but no definite shape at 25° C., like water.

Consumables

A consumable should be understood to be any compound suitable for being used in derivatisation and extraction of the metabolites.

Metabolite Profile

A metabolite profile as used in the invention should be understood to be any defined set of values of quantitative results for metabolites that can be used for comparison to reference values or profiles derived from another sample or a group of sampels. For instance, a metabolite profile of a sample from a diseased patient might be significantly different from a metabolite profile of a sample from a similarly matched healthy patient.

Metabolites can be, but not limited to, amino acids, peptides, acylcarnitines, monosaccharides, lipids and phospholipids, prostaglandins, hydroxyeicosatetraenoic acids, hydroxyoctadecadienoic acids, steroids, bile acids and glyco- and phospholipids can be detected and/or quantified.

Examples for metabolites, which can be detected and/or quantified, are listed in Table 2. In particular, lipid species from C4:X to C46:X (where X, the degree of saturation, ranges from 0 to 8) in any given fatty acid residue are shown. The lipids include also sphingolipids and glycosphingolipids.

Amino acids, which can be detected and quantified, are proteogenic or non-proteogenic amino acids. The proteogenic amino acids and the non-proteogenic amino acids, as indicated in Table 2, are preferred.

Acylcarnitines from C4:X to C18:X (wherein X is the degree of saturation and ranges from 0 to 8 in any given acid residue) can be detected and/or analyzed. Examples for acylcarnitines which are preferred are also listed in Table 2.

Monosaccharides are preferably reducing or non-reducing carbohydrates. Examples of monosaccharides are also listed in Table 2.

TABLE 2

Metabolites that are amenable to mass spectrometric analyses according to the invention Lipids:

| Abbreviation | Full name of lipid subtype Glycerophospholipids, sphingolipids and glycosphingolipids | Comments Fatty acid chain length |
|---|---|---|
| Sph | Sphingosine | None |
| Cer | Ceramide | C6:X-C36:X |
| SM | sphingomyelin | C6:X-C36:X |
| Sph pchol | sphingosylphosphorylcholin | None |
| Sph dh | dihydrosphingosine | None |
| PC | phoshatidylcholine | C4:X-C46:X |
| PI | phosphatidylinositol | C4:X-C46:X |
| PS | phosphatidylserine | C4:X-C46:X |
| PC (a) | lysophoshatidylcholine | C4:X-C32:X |
| PI (a) | lysophosphatidylinositol | C4:X-C32:X |
| PS (a) | lysophosphatidylserine | C4:X-C32:X |
| PC (e) | plasmenylphoshatidylcholine | C4:1-C32:X |
| PC (e) | plasmanylphoshatidylcholine | C4:0-C32:0 |

Amino acids

| abbreviation | Full name | Comments |
|---|---|---|
| Proteinogenic amino acids | | |
| A | Ala | Alanine |
| D | Asp | Aspartic acid |
| E | Glu | Glutamic acid |
| F | Phe | Phenylalanine |
| G | Gly | Glycine |
| H | His | Histidine |
| | Xle | Leucine/Isoleucine |
| K | Lys | Lysine |
| M | Met | Methionine |
| P | Pro | Proline |
| R | Arg | Arginine |
| S | Ser | Serine |
| T | Thr | Threonine |
| V | Val | Valine |
| W | Trp | Tryptophan |
| Y | Tyr | Tyrosine |
| | ADMA | Asymmetrical dimethyl arginine | LC MS method |
| | SDMA | Symmetrical dimethyl arginine | LC MS method |
| Q | Gln | Glutamine |
| N | Asn | Asparagine |
| | | Nitrotyrosine | LC MS method |

TABLE 2-continued

Metabolites that are amenable to mass spectometric analyses according to the invention

| | | | |
|---|---|---|---|
| | | Hydroxyproline | LC MS method |
| | | Kynurenine | LC MS method |
| | | 3-Hydroxy kynurenine | LC MS method |
| | | Non-proteinogenic amino acids | |
| O | Orn | Ornithine | |
| | Cit | Citrulline | |

Acylcarnitines

| abbreviation | Full name | Comments |
|---|---|---|
| C0 | Carnitine (free carnitine) | C0 |
| C2:X to C18:X | Acylcarnitine | C0:X to C26:X |
| C3:X-OH to C18:2-OH | Hydroxylacylcarnitine | C3-OH to C18:2-OH |
| C3:0-DC to C18:2-DC | Dicarboxylacylcarnitines | C3:0-DC to C12:0-DC |

Reducing monosaccharides

| abbreviation | Full name(s) | Comments |
|---|---|---|
| H | Hexose | |
| P | Pentose | |
| dH | Deoxyhexose | |

Others

| abbreviation | Full name | Comments |
|---|---|---|
| Cr | Creatinine | |
| | Spermidine | LC MS method |
| | Spermine | LC MS method |
| | Putrescine | LC MS method |
| | Dopamine | LC MS method |
| | Serotonin | LC MS method |
| | Prostaglandins | LC MS method |
| | Hydoxyeicosatetraeneoic (HETEs) | LC MS method |
| | Hydroxyoctadecadienoic (HODEs) | LC MS method |
| | Leukatrienes | LC MS method |
| | Thromboxanes | LC MS method |
| | Bile acids | LC MS method |
| | Sterols | LC MS method |
| | Cholesterols | LC MS method |
| | Vitamins and cofactors | |
| | Drugs and drug metabolites | LC MS method |

Drug Profile

A drug profile as used in the invention should be understood to be any defined set of values of quantitative results for one or more drugs or drug metabolites in a specific sample. Moreover, immunosuppressants as specific examples can also be detected and quantified. For example, a drug profile of a transplant patient would give the physician the immediate circulating amounts of one or more drug therapies in use, and future dosages could therefore be increased or decreased according to the quantities measured to achieve best therapeutic range. Such an analysis is designated as therapeutic drug monitoring (TDM). Immunosuppressants in accordance with the invention are to be understood as drugs that may be used in immunosuppressive therapy to inhibit or prevent activity of the immune system. Clinically they are used to prevent the rejection of transplanted organs and tissues and in treatment of autoimmune diseases such as rheumatoid arthritis, myasthenia gravis, systemic lupus erythematosus, Crohn's desease, and ulcerative colitis. Immunosuppressants as defined herein basically can be classified into four groups: glucocorticoids, cytostatics, antibodies, and drugs acting on immunophilins. Preferred examples of immunosuppressants as used in the invention are Cyclosporin A, Sirolimus, Everolimus and Tacrolimus.

Multiple Device

A multi-device as used in the invention should be understood to be any multiple devices joined together to form a multi-device such as a microtitre plate standard format.

A microtitre plate as used in the invention should be understood to be any plastic sample holder used in biology or chemistry research facilities. The microtitre plate standard was formalized by the Society for Biomolecular Screening (SBS) in 1996. It typically has 6, 24, 96, 384 or 1536 sample wells arranged in a 2:3 rectangular matrix. The standard governs well dimensions (e.g. diameter, spacing and depth) as well as plate properties (e.g. dimensions and rigidity).

The device in multiple format herein named a multi-device may also have a different format. Pre-embedding several vials, as an example, 6 wells to give a 6 point calibration with multiple calibrating compounds. Quality control samples containing known metabolites and/or multiple drug concentrations are also pre-embedded.

The device according to a preferred embodiment of the invention additionally includes a porous (or non-porous) support such as cellulose or glass fibre as examples, preferably retained in at least one well by a chemically inert retaining structure. The support preferably has embedded into it internal standards in a dry state; optionally microencapsulated (coated) with a protective or covering material or mixture of chemicals, for example polyethylene glycol 1000, phosphatidylcholine, glycerol or sorbitol.

Insert

Figure 7:
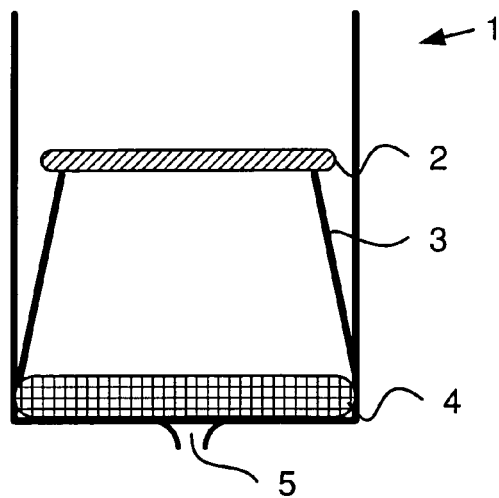
FIG. 7 describes a cross-sectional view of a singular device preferably used according to the invention containing wells or vials and its assemblage from individual components. Reference number (1) shows a well/vial. Reference number (2) shows an insert comprising an immobilising stationary phase of glass, celluloses or other suitable material (i.e. a porous support) optionally containing internal standards with optional (micro)encapsulation; reference number (3) shows a retainer to hold the porous support in the well or vial, which is chemically inert to derivatives and solvent; reference number (4) shows a filter; reference number (5) shows an outlet, which opens under pressure of centrifugal or gravitational force or vacuum.

The term "insert" as used in accordance with a particular preferred embodiment of the invention should be understood to be a porous support containing the internal standards with an optional chemical protectant as mentioned above. The insert may have any geometrical form as long as the insert fits into the well or vial of the device. In a preferred embodiment the insert is arranged within the well or vial of the device by using a retainer. The retainer is indicated as reference number (3) in FIG. 7. In a particular preferable embodiment the retainer (3) allows the insert to be arranged within the well without any direct contact between the insert and the well. Thus, the insert is located above the bottom of the well preferably within a distance of about 2 to 10 mm, more preferably of about 3 to 5 mm by using the retainer. In other words, in a preferred embodiment there is a so-called "gap" or "distance" between the bottom of the well and the insert and/or the between the walls of the well and the insert. As the retainer in the preferred embodiment any retainer is suitable as long as it allows the formation of the gap between the bottom of the well and the insert. Such an arrangment allows for maximum surface area of the support to precipitate the samples onto. The design further ensures the insert is fully accessed by flow of air or other drying gas around the insert to enable rapid drying of sample after application. This design principal also ensures the insert is fully accessed by flow of solvent from all sides enabling metabolite or drug extraction from sample with minimized protein or salt contaminants. Thus, the pores of the support allow a reaction (derivatisation) to proceed within the support itself, minimizing solvent usage and also subsequent removal as evaporation of excess derivative and solvents is provided by maximum surface area to circulating drying gases (air or nitrogen) around the sample. The increased surface area and solvent mobility around the entire support also ensures high extraction efficiencies using appropriate solvents. In other words, the above-mentioned gap allows an almost free arrangement of the insert within the well and an improved circulation of fluids flowing through the well.

Moreover, according to a preferred embodiment of the invention the device may comprise more than one insert arranged in stacks, wherein the respective inserts are more preferably arranged with the above-mentioned gap between each other in order to allow the circulation of fluids.

However, it should be understood that the invention does not necessarily comprise the insert as described above. The insert, however, is used in accordance with a preferred embodiment.

Support

The support as used in the invention may be any support preferably with at least medium degree, preferably a high degree of porosity. Such a support in principle is known in the prior art and also commercially available.

The porosity "Φ" of a medium (i.e. the support) is defined to be the proportion of the non-solid volume to the total volume of material, and is defined by the ratio:

$$\Phi = Vp/Vm$$

where Vp is the non-solid volume (pores and liquid) and Vm is the total volume of material, including the solid and non-solid parts.

Thus, porosity is a value between 0 and 1, typically ranging from less than 0.01 for solid granite to more than 0.5 for peat and clay, although it may also be represented in percent terms by multiplying the fraction by 100%. The porous support of the invention has a porosity of at least 30%, more prefably at least 50%, even more preferably at least 70%, and most preferably at least 90%.

The porous (or non-porous) support as used in the insert may be of any suitable material, but it is preferably a solid support. More preferably the porous support is comprised of a sorbent material for liquids (also named liquid sorbent material). Still more preferably the support is formed from the liquid sorbent material. The sorbent material may be an adsorbent or an absorbent material.

A liquid sorbent material as used in the invention should be understood to be any material that allows solutions of internal standards and subsequent samples for analysis to be adsorbed or absorbed uniformally throughout the pores additionally allowing carrier solvent removal by evaporation.

The liquid allowed to being ad- or absorbed by the support material can be any kind of liquid, but it is preferably a volatile liquid at atmospheric pressure. For example, a suitable liquid will have a boiling point less than about 250 degrees Centigrade (C.) at atmospsheric pressure.

More preferably, the liquid sorbent material according to the invention may be at least one of a carbohydrate material, such as cellulose material, glass fibres, glass beads, polyacrylamide gel, porous plastic inert polymer and porous graphite. The porous sorbent material may more preferably be formed from a carbohydrate material or derivative thereof, such as agarose, agar, cellulose, dextran, chitosan, or konjac, carrageenan, gellan, or alginate. The liquid sorbent material is, however, most preferably made of cellulose or glass fibres. The shape of the support or liquid sorbent material is not particularly limited but preferably is of a circular, square or scroll or nautilus dimension. According to the invention the shape of the support or sorbent material is adapted to the shape of the well or vial of the device. As mentioned, the porous support or sorbent material may be fixed or secured in its position in the well or vial by a fixing structure such as a retainer (indicated as (3) in FIG. 7).

The porous support comprising the liquid sorbent material mainly has two functions. The first is to embed the internal standards (reference material) as descibed below at predefined concentration ready for addition of the biological sample. The second is the immobilizing of the contents of each sample. This immobilizing step induces cell lysis, protein immobilisation/precipitation and salt and many other drug or metabolite retention from each of the samples. The porosity of the support is then essential for maximal exposure to both the derivatising agents and also the extraction solvent to be added for the analysis.

Encapsulation of the Standards

The internal standard in accordance with a preferred embodiment of the invention is encapsulated with a covering material or protecting material protecting the internal standard from degradation and chemical reactivity prior to use. The protection of the internal standard from degradation and chemical reactivity can prevent many forms of breakdown or chemical modification of the internal standard, such as prevention of the action of sunlight, temperature, and microorganisms, in particular prevention from any process that transforms the internal standard into breakdown or degradation products, thereby influencing the outcome of a quantitative analysis.

A protecting/covering material as used in the invention should be understood to be any material for shielding or designed to shield the internal standards) against degradation.

The protecting/covering material according to the invention can be any material suitable for protecting the internal standard from an environmental influence as mentioned above. The covering material according to the invention preferably comprises at least one of a polymer, a micelle-forming compound, a liposome-forming compound and a polyhydroxy compound, or any mixtures thereof.

If the covering material is a polymer, said polymer as used in the invention is not particularly limited and understood to be a high molecular weight organic compound, such as having a weight average molecular weight of at least about 500 g/mol or at least about 1,000 g/mol or at least about 5,000 g/mol or at least about 10,000 g/mol, which is either natural or synthetic, whose structure can be represented by a repeated small unit of a monomer. A synthetic polymer is formed in a manner known in the art such as by addition or condensation polymerization reaction of monomers. The polymer of the invention may also be a co-polymer, when two or more different monomers are involved. A homopolymer is a polymer which is formed from only one type of monomer.

The polymer according to the invention is preferably a polyalkylene glycol homopolymer or copolymer or a mixture thereof. The weight average molecular weight is preferably about 1000 daltons (Da). More preferably the polymer according to the invention is a polyethylene glycol (PEG) or polypropylene glycol (PPG), preferably PEG 1000 having a weight average molecular weight of about 1000 Da, as it is soluble or miscible with highly polar and less polar to unpolar solvents.

If the covering material is a micelle-forming compound said compound as used in the invention should be understood to be any compound which can induce submicroscopic aggregation of molecules, as droplets in a colloidal system. The micelle-forming compound according to the invention is preferably a surfactant.

A surfactant as used in the invention is understood to be any chemical compound that reduces the surface tension between two liquids; or any surface-active agent which increases the emulsifying, foaming, dispersing, spreading and wetting properties of a product, in particular any organic compound whose molecules contain a hydrophilic group at one end and a lipophilic group at the other end. Suitable surfactants include cationic, anionic, nonionic, and amphoteric surfactants. Preferably, the surfactant can be phosphatidyl (C17:0)$_2$.

If the covering material is a liposome-forming compound said compound as used in the invention should be understood to be any compound which can build artificial microscopic vesicles consisting of an aqueous core enclosed in one or more phospholipid layers, used to convey vaccines, drugs, enzymes, or other substances to target cells or organs.

A phospholipid as used in the invention is understood in the general way in the art and should comprise phosphorous containing lipid, such as lecithin and cephalin, made of glycerol and fatty acids, with a phosphate group attached. More preferably the liposome forming compound is a phospholipid, such as a phosphatidyl choline or a phosphatidyl ethanolamine or derivatives thereof.

If the covering material is a polyhydroxy compound said compound as used in the invention should be understood to comprise at least two hydroxy groups. Most preferably the polyhydroxy compound is sorbitol and/or glycerol.

Preferably the encapsulation according to the invention is a microencapsulation. A microencapsulation as used in the invention should be understood to be any encapsulation of microcapsules, which are small, preferably microscopic capsules designed to release their contents when broken by pressure, dissolved or melted. In particular, the capsules of the invention preferably have a diameter of less than about 100 micrometer, more preferably less than 10 micrometer and most preferable less than about 1 micrometer.

Microencapsulated internal standards are robust in terms of storage and shipping and are stable regarding oxidation and degradation processes, and they have a relatively long shelf-life. The microencapsulation is preferably standardized to prepare synthetic quality control material based on microencapsulated components. This is typically achieved by drying internal standards and other protected samples down with the covering material in a solvent that is a suitable solvent for these compounds like a chloroform/methanol mixture for phospholipids. Typically addition of water to these samples induces micelle and/or liposome formations to occur, and embedding of these internal or external standard lipophilic protected compounds is then made possible in water.

For example, the device is prepared as follows: The internal standard, dissolved in a suitable solvent, is pipetted in a known amount onto a porous support and dried. This procedure is repeated for every internal standard or class of internal standards to be employed in the device. If an encapsulation is provided, as the final step, the encapsulating/covering material, preferably in a suitable solvent, is put onto the support including the internal standards (i.e., the insert) and dried. The insert is then inserted into the well, preferably by using a securing means or fixing structure such as a retainer. As an alternative, the support may be inserted into the well before pipetting the internal standards and the optional covering material onto the support.

Well

A well as used in the invention should be understood to be any vial or tube consisting of a material, which is preferably solvent and derivative resistant, wherein an extraction or chemical reaction can take place. The one or more wells (indicated as (18) in FIG. 1 and (1) in FIG. 7) of the device preferably comprise at least one filter for separating micron size solids, more preferably exactly one filter for separating micron size solids (indicated as (4) in FIG. 7). The one or more wells of the device preferably comprise at least one outlet (indicated as (5) in FIG. 7) for discharging the filtrate.

A filter contained in the well as used in the invention should be understood to be any porous material a liquid or gas is passed through in order to separate the fluid from suspended particulate matter. The filter has preferably a pore size of about 50 to 0.01 micrometer, more preferably about 5 to 0.1 micrometer, and even more preferably about 1 to 0.3 micrometer. Most preferably, the filter has a pore size of about 0.45 micrometer. The filter is located in the well. Moreover, the outlet according to the invention preferably opens under applied centrifugal force or reduced pressure, preferably below about 500 mbar. The reduced pressure is preferably applied on the side of the outlet of the well. Alternatively, an increased pressure on the upper side of the well can be applied in order to ensure a flow from the well to the outlet.

Apparatus

Furthermore, the microtiter plate as described above may also be used in an apparatus for the quantitative analysis of a metabolite profile in a biological sample. Said apparatus comprises a treatment unit for preparing the metabolite to be screened comprising an automated liquid handling system, typically combined with devices for derivatisation of the metabolites present in the sample and for subsequent extraction of the derivatives; a mass spectrometer for the quantitative targeted mass spectrometry-based analysis, and a database for storing results of the analysis.

The apparatus, also called platform, as used in the invention should be understood to be any apparatus that enables the complete preparation of a biological sample ready for analysis by mass spectrometry. This encompasses processes of derivatization, desalting, concentrating and extraction. This also includes all possible combinations of some or all of these processes in a fully automated method, preferably incorporating a liquid handling system in combination with a sample centrifugal device, a sample heating and cooling device, a sample shaking device, a sample drying device, a sample pipetting device and a sample homogenization device. A liquid handling system as used in the invention should be understood to be any mechanical device that enables accurate aspiration and dispensing of many types of solvents in and out of vials and microtitre plates. A liquid handling system may be controlled by a computer and controlling software used in such a liquid handling system.

A database as used in the invention should be understood to be any collection of data arranged for ease and speed of search and retrieval.

A targeted mass spectrometry analysis as used in the invention should be understood to be mass spectrometry analysis, wherein one or more preset ion pairs are used, specifically defining and representing a known metabolite by a known fragmentation pattern that is characteristic for the corresponding analyte, for identification of the targeted metabolite. The obtained ion intensities are used together with the appropriate internal standard to calculate the concentration of the targeted metabolite. The internal standard is identified by using a characteristic ion pair (or several), their obtained ion intensities are related to the known concentration of the internal standard allowing the quantification of a corresponding targeted metabolite. The set of targeted metabolites is known in advance and can be pre-annotated. Therefore, detected and quantified metabolites are already annotated allowing a fast and direct interpretation. A tandem mass spectrometer is particularly preferred as a mass spectrometer capable of MSMS analyses to distinguish more specifically ion species. Preferably, the apparatus allows for automated standardized sample preparation and high-resolution tandem mass analytics procedures. In particular, the automated sample preparation procedure increases day to day reproducibility of reliable results and lower coefficients of variance (CVs). When, for example, analyzing a derivatized sugar with a precursor ion scan, the derivative itself can be detected by the mass spectrometer. In positive ion mode this is preferably the formation of the phenylmethylpyrazolone (PMP) (MH)+ion at m/z 175. The composition of the carbohydrate itself or discret isomers are detectable.

Standard Operation Procedure (SOP)

SOP's are detailed, written instructions with the objective to guarantee high quality and uniformity of the performance of metabolite analysis. In this context, all the working and processing steps with corresponding parameters, such as for sample processing, mass spectrometry analysis and data processing are defined facilitating a standardized metabolite sample collection, handling, preparation, analysis and data processing, which leads to reproducible results with low intra and inter day variability. Typically, a specific SOP relates to the analysis of one ore more metabolite classes for one or more sample material types.

Parameter Set

All the steps and corresponding parameters of the SOP are stored and managed in a data base. After one or several SOPs are assigned to a sample or sample collection (i.e. samples on a mircotiter plate), all parameters for sample preparation are send to the control unit to manage and monitor the sample preparation process in the treatment unit. All steps, including pipetting, derivatisation, incubation and extraction, are controlled by the corresponding parameter set. The mass spectrometry (MS) analysis is controlled in a similar way by the control unit applying the corresponding parameters of the parameter set. The parameters define the MS—method, such as scan times and positive or negative ionisation for multiple reaction monitoring (MRM), precursor and neutral loss scans. Furthermore, all the parameters for identification of targeted metabolites and related internal standards, such as mass pairs and mass tolerances, and for quantification, such as concentration of internal standards, response factors, detection limit and linear range are included in the parameter set.

Filtering

Data processing involves typically the data reduction step called filtering. Noise filters reduce the data based on a calculated noise threshold. In this respect, data below a certain signal to noise ratio is filtered. Content based filtering of the results leverages, for example, disease specific knowledge to concentrate on relevant metabolic aspects of the disease under investigation.

Comparing and Evaluation

After pre-processed data derived from mass spectrometry analysis has been technical validated, statistical analysis can proceed. Depending on the design of a metabolite profiling study a sample or several samples derived from healthy controls and patients are compared to reveal differences, i.e. biomarkers that can be utilized to characterize a disease at the molecular level. In another embodiment, samples are derived from patients participating in a clinical trial, where a novel drug compound is under investigation and compared to an approved drug. Evaluation of metabolite profiling shows the pharmacodynamic profiles and difference of the investigates compounds or dosages. These pharmacodynamic profiles point to the efficacy and side effects caused by the individual compounds.

In the following, an exemplary configuration of an apparatus according to the invention is described. Referring to FIG. 1, the apparatus 10 includes a treatment unit 11 and the mass spectrometer 14. Further, there is a controlling unit 12 coupled to an input unit 16. The controlling unit 12 is connected to a database 13. The database 13 is coupled to an evaluation/comparison and output unit 20. The database 13 receives results of a processing unit 15. The processing unit 15 receives the results from the mass spectrometer 14. The prcessing unit 15 may be combined with the controlling unit 12 or may be realized as separate unit.

Figure 2:
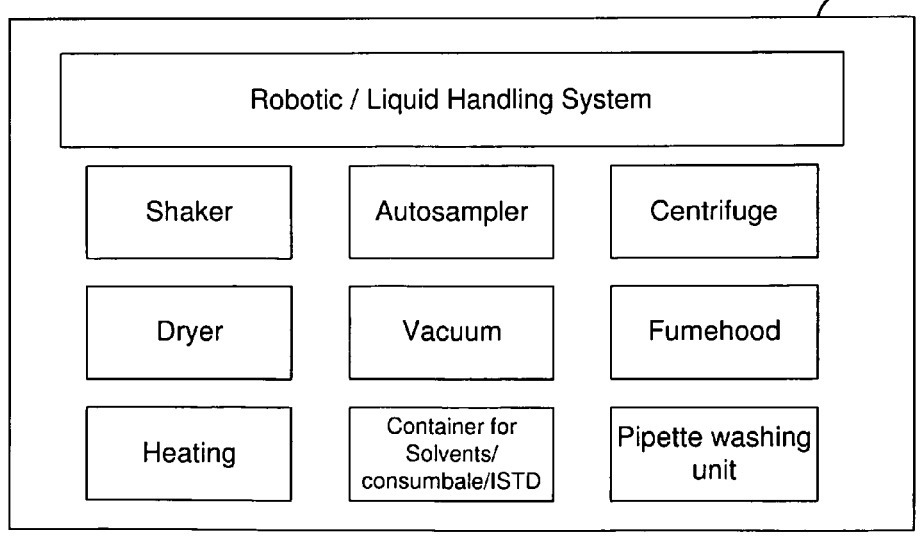
FIG. 2 shows a schematic diagram illustrating components of the treatment unit according to the invention.

In the following, the components of the treatment unit 11, as shown in FIG. 2, are described in more detail. The treatment unit 11 includes a robotic system, which is handling the microtiter plate 22. Further, it is handling the introduction of internal standards, consumables or solvents into the wells of the microtiter plate 22. The treatment unit 11 includes a liquid handling system. The treatment unit 11 further includes an auto sampler, which divides the biological sample into a plurality of aliquots, which are provided in the wells of the microtiter plate 22.

In one embodiment of the invention the microtiter plate 22 includes aliquots, which are derived from one biological sample only. However, it is also possible to have different biological samples, which are distributed in different wells of the microtiter plate 22.

The treatment unit 11 further includes containers including different internal standards, consumables or solvents. The robotic system is accessing the different containers for adding the internal standards, consumables or solvents to the respective aliquots in the wells.

Further components are required for preparing the plurality of combined aliquots. It may be required to put the aliquots under vacuum or under pressure. Additionally, a shaker and/or a centrifuge are arranged for providing a reliable mixing of the internal standards, consumable and solvents with the aliquots. Additional components of the treatment unit are, for instance, the fume hood and the pipette washing unit.

The microtiter plate 22 includes an upper and a lower plate, which may be separated from each other after the treatment of the combined samples in the treatment unit 11. The upper plate has a holder or retainer for holding a support, which maybe impregnated with one or more internal standards, consumables or solvents.

Instead of supplying the internal standards, consumables or solvents in liquid form they may be provided before on the porous support. The porous support may be inserted in the well in the upper plate. Thus the aliquots of the biological sample may solubilize the internal standards, consumables or solvents during treatment.

Figure 3:
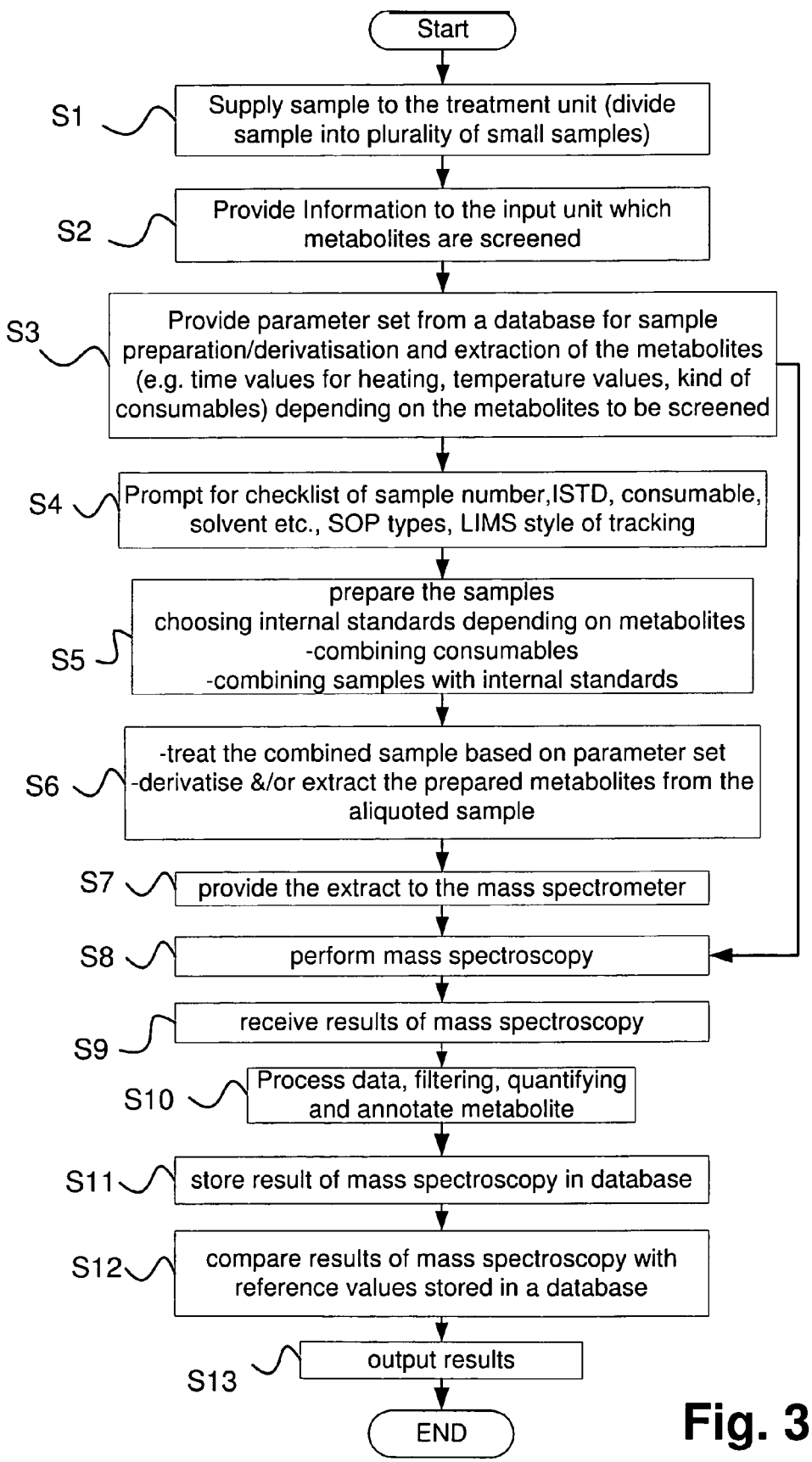
FIG. 3 shows a simplified flowchart according to the method of the invention.

In the following the method for analyzing the metabolite profile in a biological sample is explained based on FIG. 3.

In step S1 the biological sample to be investigated, e.g. blood of a healthy person, is supplied to the treatment unit 11, where it is divided into multiple aliquots 18$n$ by use of an autosampler. The aliquots are supplied to the wells of the microtiter plate 22 having 96 wells. The microtiter plate 22 is then moved by the robotic system to a place for inserting internal standards, consumables or solvents. The determination, which internal standards, consumables or solvents need to be combined with a certain aliquot, is performed based on the information, which metabolites have to be screened. In particular by assigning the SOP and the corresponding parameter set to a sample or sample collection, —the way to handle the sample(s) is defined and standardized.

In step S2 information, which metabolites have to be screened, is inputted via the input unit 16, which is supplied to the controlling unit 12. Based on this information the controlling unit 12 determines the parameter set/SOP, which is used for the sample preparation, separation and for mass spectrometry analysis of the respective combined and separated biological samples. The parameter set reflects the processing steps and parameters of the corresponding standard operational procedure (SOP). The controlling unit 12 accesses the database 13 containing data of the parameter sets/SOPs required for treating a biological sample and for performing the mass spectrometry analysis. By deriving a parameter set/SOP out of the database 13 the controlling unit 12 determines how to perform the sample preparation, derivatization and extraction of metabolites. This parameter set may include time values for treating, temperature values for heating and the kind of consumables/solvents, which should be combined with certain samples, etc.

The user may be asked to input project and sample related information into a laboratory information management system (LIMS), define work list with the unique sample identifiers, barcodes and assign the standard operation procedures (SOP). The LIMS can be utilized for tracking the biological samples during the preparation, the treatment and mass spectrometry analysis and for quality control and management. In one embodiment, the LIMS can comprise the input, control, processing and evaluation unit and database, but can also be realized as separate unit with interfaces to the other units.

In step S5 the aliquots 18n of the biological sample are combined with at least one of an internal standard, consumable and solvents. In particular, it is possible to combine different consumables/solvents to each aliquot.

After being combined the plurality of combined samples or aliquots are treated in step S6 depending on the metabolites to be screened. The information which kind of metabolite has to be screened is inputted in the input unit 16, for example, by a user. It is further possible to input the information which metabolites have to be screened by an automated reading device which reads, for instance, a barcode on the device containing the biological sample before or during supplying to the treatment unit 11. The barcode indicates which metabolites have to be screened. The treatment is performed in the liquid handling system, which may include extraction according to polarity of solvent mixtures, adding of sample, drying of sample on porous support, derivatization, drying and extraction by centrifugation (or vaccum). After the treatment the upper plate of the microtiter plate 22 is removed. The lower plate contains the extracted metabolites, which are provided to the mass spectrometry analysis.

In step S7 the extract of each aliquot 18n is provided separately to the mass spectrometer 14 by use of an auto sampler.

In step S8 the mass spectrometry is performed. The mass spectrometry analysis is controlled in a similar way by the control unit applying the corresponding parameters of the parameter set 14. The parameters define the MS-method, such as scan times and positive or negative ionisation for multiple reaction monitoring (MRM), precursor and neutral loss scans. Furtermore, all the parameters for identification of targeted metabolites and related internal standards, such as mass pairs and mass tolerances, and for quantification, such as concentration of internal standards, response factors, detection limit and linear range are included in the parameter set. In step S9 the result of mass spectrometry analysis are received.

As explained above, each extract of an aliquot sample is separately provided to the mass spectrometry analysis. Thus, the steps S7 to S9 are performed 96 times since there are 96 wells in a microtiter plate 22.

The results are received in the processing unit 15. In the processing unit 15 step S10 is performed including the processing of data, which includes noise filtering, content based filtering of the results, quantification, and annotation of the detected metabolites. The processed and filtered results are stored in a database 13 in step S11. The processing unit 15 detects the targeted metabolites and corresponding internal standards and calculates the concentrations of the metabolites, as the concentrations of the internal standard of a respective sample 18n are known. After calculation of the concentrations the filtering is performed. Since there is a huge amount of mass spectrometry data, the derived results need to be filtered, wherein different filtering methods may be applied to reduce the amounts of data. Then the filtered data are stored. After having stored the prepared or processed results of the mass spectrometry analysis the results can be compared to reference values, which are stored in the database 13 in step S12 to derive information, which indicate a normal or pathogenic disease state or the pharmacological response to therapeutic intervention.

The results are outputted in step S13 by use of a monitor or a printout. Based on the information, which may be derived during comparing the results of the mass spectrometry with reference values stored in a database 13, the database may be updated. This learning process may be used for providing an adaptation of the parameter sets, which are used for treating the biological samples for analyses of the metabolites profile.

Figure 4:
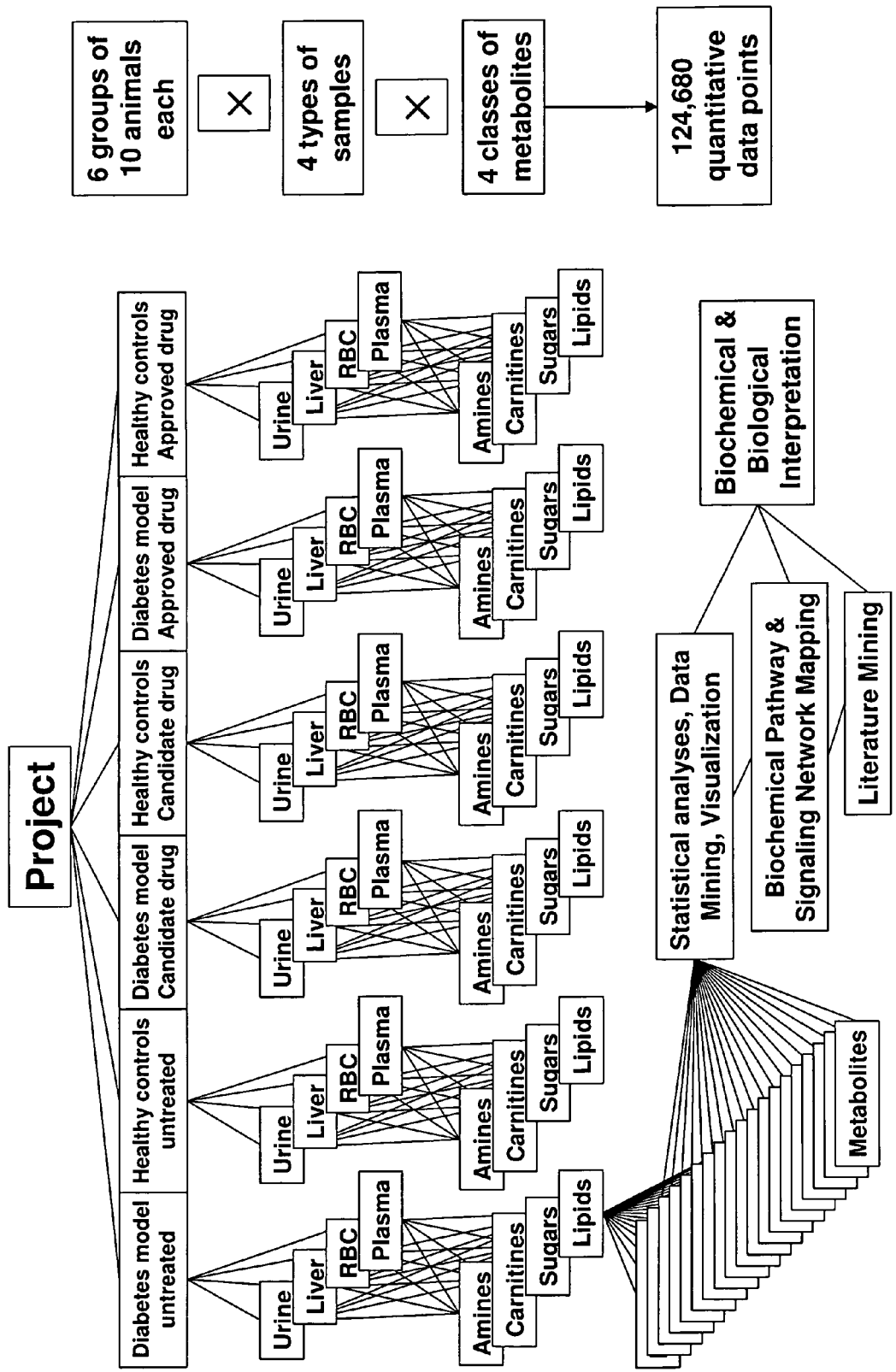
FIG. 4 shows a schematic overview for a pre-clinical trial which uses the inventive method and the apparatus.

With reference to FIG. 4 an example will be given for deriving multiple results for creating a metabolite profile of a biological sample.

A pre-clinical trial on diabetes mellitus type II exploiting a qualitative and quantitative metabolite profiling approach was conducted for metabolic characterization of a disease mouse model and detailed pharmacodynamic description of a novel candidate drug class. Six groups were studied composed of healthy and diseased mice that were either treated, untreated or treated with an approved drug.

The six groups are in the first row including a diseased group (T2D), healthy group, a drug candidate treated diseased group, a drug candidate treated healthy group, a diseased group treated with an approved drug and a healthy group treated an approved drug. For each group a predetermined number of animals are tested. For each animal four materials are used as biological samples. In this embodiment, a urine sample, a plasma sample, a red blood sample and a liver sample are taken from each animal. Each sample is provided in the inventive apparatus and is tested on four different classes for metabolites. Each class of metabolites (amines, carnitines, sugars, lipids) is characterized by a specific standard operational procedure (SOP). It is noted that for analyzing red blood a different procedure is required than for testing urine. Further, the internal standards, consumables and solvents to be combined are different. Finally, the treatment and separation of the combined aliquots is different. However to perform a substantiated test each sample of each group is screened by use of four different SOPs.

After performing the whole test procedure more than 120,000 quantitative features of these tests are derived. These quantitative features need to be analyzed by using statistical procedures. Additionally, by using a knowledge database, data mining can be performed.

Figure 5:
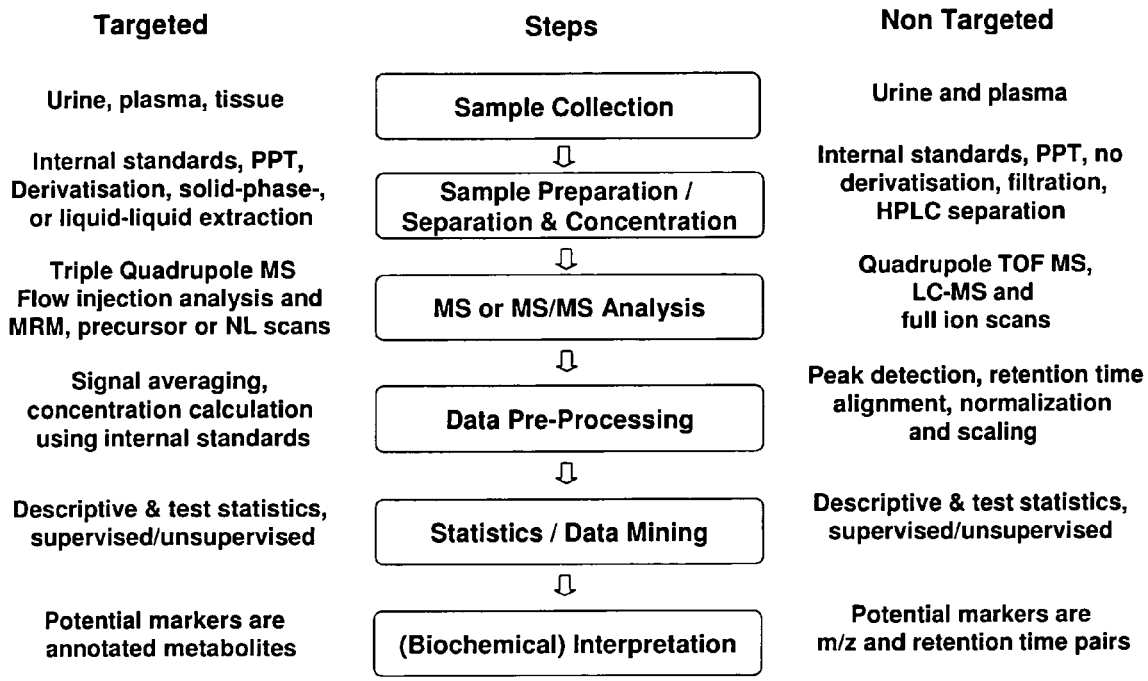
FIG. 5 shows a schematic illustration for comparing non-targeted and targeted metabilte profiling according to the invention.

For deriving information for qualitative LC-MS metabolite profiling, mouse urine and plasma samples were separated by reversed phase chromatography, and analyzed with a quadrupole time of flight (qTOF) mass spectrometer equipped with an electrospray source. Raw spectra were filtered, aligned, and scaled, followed by statistical analysis of the data. As to quantitative targeted MS/MS analysis, mouse urine, plasma, erythrocytes and liver samples were derivitized (amino acids, acylcarnitines, sugars) and extracted by solid-phase or in Folch solution (glyco- and phospholipids) with a liquid-handling-system, and analyzed by flow injection in combination with multiple reaction monitoring (MRM), precursor and neutral loss scans with a triple quadrupole (QqQ) MS equipped with an electrospray source. Concentrations were calculated from the raw MS spectra, filtered, normalized (to creatinine, total protein), and scaled, succeeded by statistical analysis and biochemical interpretation of the pre-annotated metabolites. The procedure is illustrated in FIG. 5.

The quantitative targeted metabolite profiling concentrates on analytes (internal standards) that are pre-defined, pre-annotated, and detected by MRM, precursor and neutral loss scans. Flow injection analysis (FIA) allows signal averaging over a steady stream of ion (TIC) leading to robust signals. Characteristic mass transitions are used for identification of metabolites and associated internal standards (ISs). De-isotoping is used for protein analysis. However, isotope correction is also recommended for certain small molecule compounds and classes. These algorithms utilize calculated isotope percentages of targeted analytes to correct the measured peak intensities for their isotopic overlap. Finally, metabolite concentrations are calculated by relating the known concentrations of internal standards with the measured ion counts per second (cps).

The inventive targeted metabolite profiling methodology utilized in a liquid-handling-system for fully automated and parallel sample preparation in microtiter format guaranteeing high reproducibility and low coefficients of variation (CVs). Furthermore, analytes and corresponding metabolites were annotated in advance so as to enable fast and direct biochemical and biological interpretation.

Up to 825 metabolites were obtained from each compartment and comparison of the groups enabled identification of the animal disease model and facilitated the immediate biochemical characterization of drug effects.

Figure 6:
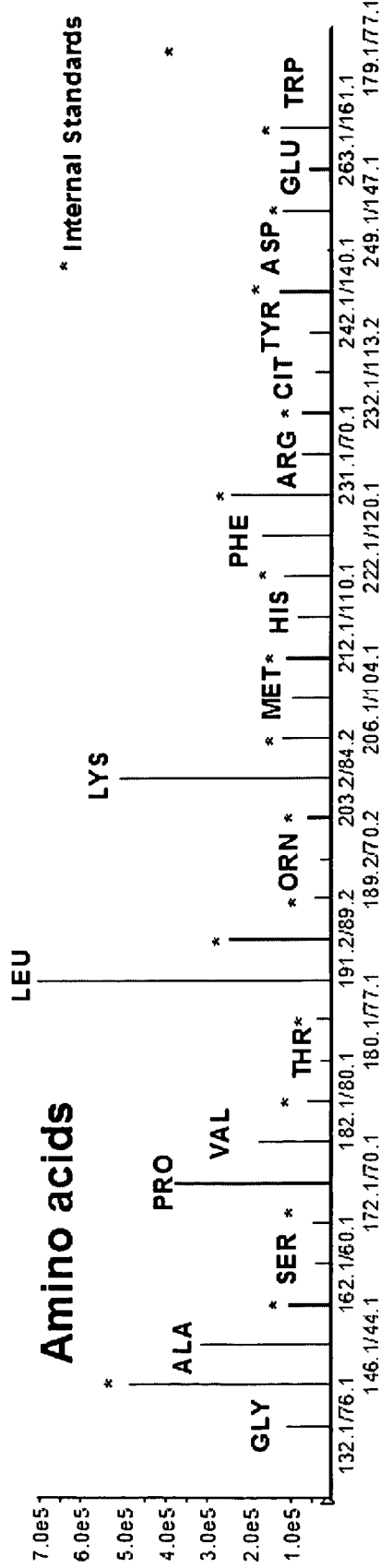
FIG. 6 illustrates results of a mass spectrometry for metabolites and internal standards according to the invention using targeted metabolite profiling.

FIG. 6 illustrated the result of mass spectrometry, wherein different amino acids are shown in comparison with peaks of known internal standards (indicated with *).

Targeted metabolite concentration profiling facilitates higher throughput and the versatility for standardized analysis of various biofluids and tissues, which is especially important for comprehensive disease characterizations, and efficacy and toxicity assessments in animal model experiments. Direct or surrogate, uni or multivariate markers are revealed by data mining techniques with the objective to describe diseases at the molecular level, which are subsequently often used to study metabolic and pharmacodynamic changes in various compartments and organs.

In general, the identical technology can be applied in various stages of pharmaceutical development, ranging from cell-based systems, and animal models to clinical studies. For example, putative biomarkers discovered and verified in the preclinical phase, such as for the characterization of normal biological and pathogenic processes or pharmacological responses to a therapeutic intervention can be clinically validated with the same analytical technology in human studies. In an intended diagnostic application, clinical studies will have to assess the predictive performance and generalization power of candidate biomarkers in clinical routine, where typically high specificity is required to rule out other diseases.

Each successful metabolite profiling biomarker discovery study relies on a carefully planned experimental design with clear defined objectives, a detailed plan and quality control procedures in advance, as is common practice in controlled clinical trials. Well thought-through experimental designs maximize the information obtained for a given experimental effort, yielding to valid and objective conclusions.

Experimental flaws and bias jeopardizes the predictive performance and generalization power of statistically determined biomarkers. In this context, metabolite profiling has to learn from the past, where insufficient experimental design and deficient reproducibility in early clinical validation studies have restrained the widespread use of serum protein profiling technologies.

Of course, beyond statistical significance lies the problem of biological significance. Just because an expression or concentration change is statistically significant does not always imply that the change has any affect on the underlying biology. Some genes, protein or metabolites are tightly regulated so that small changes in abundance are biologically relevant, while others are loosely regulated and can vary considerably with no biological effect.

In summary, when carrying out the analysis of a metabolite profile according to the invention a quantity of hundreds of metabolites can be analyzed simultaneously from microtitre quantities of biological material with high speed, precision and sensitivity using pre-analytical steps. Quality assured (QA) data is generated from individual samples in the matter of minutes and interpreted employing cutting edge statistical software tools. This method also overcomes hitherto to existing analytical bottlenecks through pre-analytical standardization and automation, and user-friendly statistical and biochemical data interpretation. This integration of all components in the method of the invention into a new technology platform will make "biochemical fingerprinting" accessible for widespread application and will expedite the spread of metabolomics.

EXAMPLES

The invention will be further illustrated by the following non-limiting examples.

Preparation and Conditions of the Multi-Device

One multi-device was prepared using 7 mm cellulose spots (cut from generic card—10 539 859, Schleicher Schuell Biosciences GmbH, Dassel, Germany) as the porous support in each of the 96 wells of a Solvinert microtitre plate (MSRP N04, Millipore Corp. MA, USA). These were fixed into place with manufactured retainers made from polypropylene (Biocrates, Tirol, Austria).

To analyse a selected subset of metabolites, in this case, amino acids, acylcarnitines and phospholipids from a sample, a selection of suitable internal standards of amino acids, acylcarnitines and lipids labelled with stable isotopes to represent all the twenty proteogenic phosphatidylcholines, sphingomyelins, and lyso species of each were used. These were pre-embedded into the porous support of the multi-device by pipetting known amounts of each internal standard class, allowing each to dry within the porous support before adding the next mixture of internal standards, allowing to dry and so forth. In this example there were added acylcarnitines followed by amino acids and last, a mixture of phospholipid internal standards in a water solution containing 0.1% w/w polyethyleneglycol 1000 (PEG 1000), a compound which served dual purposes. As a surfactant, PEG 1000 resides in the pores of the porous support coating all internal standards offering a protective barrier to otherwise degradative actions of exposure to oxygen and water.

When completely dry the multi-device technical validation samples were then added to the first five wells of the multi-device.

Well 1: a blank,

Wells 2 and 3: control mixtures of unlabelled metabolites,

Well 4: a quality control with low concentration metabolites (normal levels or 1 times), and Well 5: a quality control with high concentration metabolites (levels 10 times normal).

The multi-device containing pre-imbedded internal standards with additional control samples in wells 1 to 5 is then stored ready to use at 4° C.

Method of Using the Multi-Device

Example 1

For examplary purposes only, the following is a description of how the device as specified above is used to process samples for analysis of a selection of metabolites.

To analyse a subset of metabolites, amino acids, acylcarnitines and phospholipids from a sample, a selection of suitable internal standards of amino acids, acylcarnitines and lipids, stable isotope labelled to represent all the twenty proteogenic amino acids, the most abundant acylcarnitines and phospholipids including phosphatidylcholines, sphingomyelins, and lyso species of each were used. Upon addition of a predefined amount of sample, typically 10 µl of plasma, the internal standards and amino acids of the sample are mixed within the confines of the pores of the insert. Any subsequent treatment that causes loss or degradation of metabolites will therefore be correlated for by the internal standard. Derivatization of the amino acids can then take place within the confines of the pores of the insert. The derivatizing reagent in this example is 15 µl of a 5% phenylisothiocyante in a 1:1:1 solution of pyridine, water, ethanol. This derivatization process occurs at room temperature in less than 20 minutes. As the derivatizing solution is completely volatile it can be simply removed under a gentle stream of nitrogen or vacuum at room temperature. The addition of a methanol solution containing 10 mM ammonium acetate extracts the derivatized amino acids, acylcarnitines and the phospholipids simultaneously from the porous device into the methanol solvent. The microtitre plate of choice for this purpose has additional properties. It has a 0.45 micron filter and a liquid outlet, that only opens under centrifugal force or vacuum, built into the bottom of each well. The methanol extract from the sample is then simply collected via centrifugation into a capture-microtitre plate, placed under the microtitre plate containing device. Mass spectrometry analysis of the solution from each well can then take place, typically using an autosampling instrument to deliver the sample to the mass spectrometer.

Example 2

The following will demonstrate that the device can be used to process samples for analysis of a selection of metabolites.

The multi-device upon accurate addition of 10 µl of blood samples from one patient to each well is mixed with the internal standards within the confines of the pores of the porous support (insert). Any subsequent treatment that causes loss or degradation of metabolites will therefore be correlated to the internal standard. Derivatization was carried out as in Example 1 and the resulting solutions from each well are then analyzed by mass spectrometry methods, typically using an autosampling instrument to deliver the sample to the spectrometer.

Results from the mass spectrometric measurements of the metabolites derivatized and extracted with the multi-device are graphically depicted in FIG. 8 and FIG. 9 showing the amino acids, the phospholipids and the acylcarnitines, respectively.

The quantities of the amino acids and acylcarnitine metabolites are shown in Table 3, also showing the accuracy and the variance of the values obtained using the multi-device.

TABLE 3

The quantities accuracy and reproducibility of the amino acids, lipids, lactate, creatinine and glucose from a single sample measured 10 times are shown in Table 3 and were obtained using the multi-device.

| Amino Acids | | | | | | | | | | | | | | |
|---|---|---|---|---|---|---|---|---|---|---|---|---|---|---|
| Sample Name | QAlow C2 | QAlow C3 | QAlow C4 | QAlow C5 | QAlow C6 | QAlow C7 | QAlow C8 | QAlow C9 | QAlow C10 | QAlow C11 | QAlow C12 | mean [µmol/l] | std | CV [%] |
| Arginine-PTC | 64.8 | 71.0 | 67.5 | 68.7 | 62.3 | 63.1 | 67.9 | 65.6 | 67.4 | 66.5 | 63.7 | 66.2 | 2.6 | 4.0 |
| Phenylalanine-PTC | 74.0 | 71.6 | 72.1 | 81.5 | 70.1 | 69.2 | 70.4 | 73.6 | 72.5 | 72.9 | 76.2 | 73.1 | 3.4 | 4.7 |
| Proline-PTC | 114.4 | 117.1 | 124.5 | 120.4 | 120.2 | 120.6 | 137.2 | 118.2 | 127.5 | 126.3 | 120.6 | 122.5 | 6.2 | 5.1 |
| Lysine-PTC | 102.2 | 94.4 | 108.4 | 110.5 | 93.0 | 102.1 | 102.1 | 98.1 | 98.9 | 101.8 | 102.1 | 101.2 | 5.2 | 5.1 |
| Histidine-PTC | 90.0 | 97.0 | 95.4 | 89.4 | 93.0 | 89.2 | 97.7 | 82.5 | 88.5 | 95.3 | 100.6 | 92.6 | 5.2 | 5.6 |
| Tryptophane-PTC | 35.8 | 39.0 | 42.7 | 38.2 | 36.6 | 36.6 | 37.4 | 38.9 | 34.8 | 34.8 | 35.7 | 37.3 | 2.3 | 6.2 |
| Tyrosine-PTC | 93.4 | 99.9 | 95.7 | 92.7 | 94.8 | 103.7 | 95.2 | 97.7 | 86.1 | 87.4 | 83.6 | 93.6 | 6.0 | 6.4 |
| x-Leucine-PTC | 174.5 | 181.2 | 158.1 | 191.9 | 164.1 | 153.8 | 167.5 | 157.2 | 150.2 | 158.6 | 157.1 | 164.9 | 12.8 | 7.8 |
| Valine-PTC | 117.0 | 96.9 | 108.7 | 121.7 | 116.3 | 114.6 | 115.7 | 134.2 | 111.7 | 116.9 | 121.0 | 115.9 | 9.1 | 7.9 |
| Ornithine-PTC | 78.7 | 81.7 | 58.8 | 67.9 | 69.3 | 68.9 | 71.6 | 68.9 | 74.8 | 74.9 | 74.4 | 71.8 | 6.2 | 8.6 |
| Methionine-PTC | 44.4 | 38.2 | 34.9 | 41.5 | 44.7 | 38.8 | 37.8 | 43.2 | 36.2 | 36.0 | 36.3 | 39.3 | 3.6 | 9.1 |
| Citrulline-PTC | 28.3 | 24.8 | 28.0 | 23.5 | 20.6 | 25.2 | 26.1 | 25.0 | 28.0 | 29.4 | 25.8 | 25.9 | 2.5 | 9.7 |
| Glutamine-PTC | 455.8 | 455.6 | 445.7 | 364.4 | 352.0 | 372.8 | 369.0 | 374.2 | 322.0 | 355.7 | 369.1 | 385.1 | 45.6 | 11.8 |
| Serine-PTC | 182.1 | 153.7 | 176.7 | 177.1 | 191.9 | 188.5 | 173.4 | 137.8 | 132.6 | 134.0 | 154.9 | 163.9 | 22.1 | 13.5 |
| Threonine-PTC | 21.3 | 26.0 | 31.0 | 34.4 | 23.5 | 29.5 | 25.7 | 29.4 | 25.0 | 24.2 | 29.0 | 27.2 | 3.8 | 14.0 |
| Alanine-PTC | 219.6 | 316.7 | 227.8 | 282.3 | 298.7 | 267.5 | 205.8 | 177.8 | 203.0 | 245.4 | 210.9 | 241.4 | 44.4 | 18.4 |
| Asparagine-PTC | 236.4 | 250.9 | 204.5 | 179.4 | 168.4 | 136.5 | 170.1 | 192.4 | 230.5 | 206.7 | 157.0 | 193.9 | 35.7 | 18.4 |
| Glycine-PTC | 320.9 | 282.0 | 272.0 | 297.9 | 412.6 | 422.9 | 252.8 | 268.5 | 225.1 | 226.8 | 278.0 | 296.3 | 66.2 | 22.4 |
| Glutamic Acid-PTC | 2115.4 | 1508.6 | 1694.6 | 1220.8 | 2118.8 | 1560.0 | 2137.9 | 2770.8 | 2137.9 | 1563.6 | 1984.8 | 1892.1 | 431.0 | 22.8 |

| Acylcarnitines | | | | | | | | | | | | | | |
|---|---|---|---|---|---|---|---|---|---|---|---|---|---|---|
| Sample Name | QAlow C2 | QAlow C3 | QAlow C4 | QAlow C5 | QAlow C6 | QAlow C7 | QAlow C8 | QAlow C9 | QAlow C10 | QAlow C11 | QAlow C12 | mean [µmol/l] | std | CV [%] |
| C2 | 8.487 | 9.674 | 9.529 | 9.007 | 8.845 | 9.105 | 9.847 | 9.477 | 9.928 | 8.552 | 9.137 | 9.24 | 0.49 | 5.4 |
| C18:1 | 0.161 | 0.233 | 0.218 | 0.216 | 0.193 | 0.193 | 0.207 | 0.225 | 0.205 | 0.191 | 0.180 | 0.20 | 0.02 | 10.4 |
| C8:1 | 0.161 | 0.233 | 0.218 | 0.216 | 0.193 | 0.193 | 0.207 | 0.225 | 0.205 | 0.191 | 0.180 | 0.20 | 0.02 | 10.4 |
| C0 | 38.351 | 48.949 | 51.179 | 53.867 | 53.869 | 52.218 | 61.745 | 60.195 | 56.018 | 52.762 | 56.524 | 53.24 | 6.21 | 11.7 |

TABLE 3-continued

The quantities accuracy and reproducibility of the amino acids, lipids, lactate, creatinine and glucose from a single sample measured 10 times are shown in Table 3 and were obtained using the multi-device.

| | | | | | | | | | | | | mean | std | CV |
|---|---|---|---|---|---|---|---|---|---|---|---|---|---|---|
| C12-DC | 0.021 | 0.015 | 0.017 | 0.013 | 0.015 | 0.017 | 0.015 | 0.017 | 0.016 | 0.017 | 0.017 | 0.02 | 0.00 | 12.4 |
| C14:2 | 0.041 | 0.050 | 0.044 | 0.035 | 0.047 | 0.052 | 0.041 | 0.050 | 0.035 | 0.047 | 0.045 | 0.04 | 0.01 | 13.1 |
| C8 | 0.232 | 0.306 | 0.352 | 0.274 | 0.200 | 0.212 | 0.264 | 0.250 | 0.258 | 0.276 | 0.299 | 0.27 | 0.04 | 16.4 |
| C12 | 0.043 | 0.051 | 0.071 | 0.047 | 0.043 | 0.043 | 0.044 | 0.048 | 0.046 | 0.045 | 0.055 | 0.05 | 0.01 | 16.7 |
| C12:1 | 0.028 | 0.025 | 0.030 | 0.031 | 0.027 | 0.035 | 0.035 | 0.030 | 0.040 | 0.034 | 0.019 | 0.03 | 0.01 | 18.6 |
| C16:1 | 0.038 | 0.016 | 0.036 | 0.037 | 0.030 | 0.035 | 0.030 | 0.033 | 0.024 | 0.030 | 0.035 | 0.03 | 0.01 | 20.2 |
| C3 | 0.293 | 0.401 | 0.524 | 0.376 | 0.274 | 0.324 | 0.309 | 0.435 | 0.423 | 0.473 | 0.423 | 0.39 | 0.08 | 20.5 |
| C14:1 | 0.110 | 0.106 | 0.103 | 0.113 | 0.113 | 0.141 | 0.174 | 0.118 | 0.172 | 0.108 | 0.117 | 0.13 | 0.03 | 20.6 |
| C4:1 | 0.110 | 0.106 | 0.103 | 0.113 | 0.113 | 0.141 | 0.174 | 0.118 | 0.172 | 0.108 | 0.117 | 0.13 | 0.03 | 20.6 |
| C7-DC | 0.050 | 0.036 | 0.044 | 0.052 | 0.040 | 0.039 | 0.066 | 0.055 | 0.036 | 0.064 | 0.041 | 0.05 | 0.01 | 22.5 |
| C5-M-DC | 0.192 | 0.204 | 0.184 | 0.202 | 0.191 | 0.209 | 0.210 | 0.316 | 0.177 | 0.136 | 0.160 | 0.20 | 0.05 | 22.7 |
| C4-OH | 0.106 | 0.080 | 0.100 | 0.167 | 0.138 | 0.129 | 0.170 | 0.151 | 0.175 | 0.115 | 0.121 | 0.13 | 0.03 | 23.7 |
| C11 | 0.006 | 0.008 | 0.010 | 0.010 | 0.013 | 0.008 | 0.010 | 0.007 | 0.012 | 0.008 | 0.006 | 0.01 | 0.00 | 23.9 |
| C16 | 0.136 | 0.204 | 0.188 | 0.169 | 0.127 | 0.096 | 0.132 | 0.137 | 0.100 | 0.124 | 0.178 | 0.14 | 0.04 | 24.6 |
| C4:1-DC | 0.148 | 0.182 | 0.241 | 0.167 | 0.111 | 0.097 | 0.165 | 0.146 | 0.226 | 0.127 | 0.218 | 0.17 | 0.05 | 28.3 |

Lipids

| Sample Name | QAlow C2 | QAlow C3 | QAlow C4 | QAlow C5 | QAlow C6 | QAlow C7 | QAlow C8 | QAlow C9 | QAlow C10 | QAlow C11 | QAlow C12 | mean [μmol/l] | std | CV [%] |
|---|---|---|---|---|---|---|---|---|---|---|---|---|---|---|
| GPCho 36:3a | 190.12 | 219.29 | 195.68 | 224.00 | 250.66 | 236.77 | 231.16 | 199.46 | 207.93 | 210.60 | 198.76 | 214.9 | 19.2 | 8.9 |
| SM d18:1/16:0 | 311.11 | 387.86 | 330.25 | 339.33 | 346.71 | 381.94 | 419.57 | 307.61 | 337.20 | 348.34 | 380.74 | 353.7 | 34.8 | 9.8 |
| GPCho 36:2e | 22.84 | 25.00 | 20.99 | 22.67 | 21.71 | 21.29 | 23.19 | 23.91 | 27.44 | 19.20 | 21.12 | 22.7 | 2.2 | 9.9 |
| GPCho 32:1a | 55.79 | 50.54 | 58.33 | 55.17 | 58.33 | 67.42 | 64.89 | 62.50 | 67.03 | 56.25 | 48.00 | 58.6 | 6.4 | 10.9 |
| GPCho 32:0a | 7.69 | 7.37 | 7.73 | 5.20 | 7.87 | 6.71 | 7.82 | 6.63 | 7.74 | 9.23 | 7.07 | 7.4 | 1.0 | 13.6 |
| LGPCho 18:2a | 6.17 | 6.43 | 6.17 | 6.00 | 8.55 | 6.45 | 6.52 | 4.35 | 7.93 | 7.28 | 6.21 | 6.6 | 1.1 | 16.7 |
| GPCho 34:1p | 76.84 | 76.34 | 87.50 | 93.10 | 73.96 | 82.02 | 80.85 | 127.50 | 82.42 | 83.33 | 82.00 | 86.0 | 14.7 | 17.2 |
| GPCho 36:1p | 243.16 | 268.82 | 354.16 | 327.59 | 300.00 | 277.53 | 288.30 | 425.00 | 290.11 | 269.79 | 259.00 | 300.3 | 51.8 | 17.3 |
| LGPCho 18:1p | 160.00 | 174.19 | 215.28 | 168.97 | 165.62 | 180.90 | 156.38 | 257.50 | 180.22 | 138.54 | 164.00 | 178.3 | 32.4 | 18.2 |
| LGPCho 18:0e | 40.24 | 47.37 | 51.38 | 43.35 | 47.19 | 65.10 | 53.63 | 59.64 | 50.97 | 67.69 | 37.88 | 51.3 | 9.7 | 18.8 |
| GPCho 38:1a | 18.95 | 21.51 | 29.17 | 17.24 | 25.00 | 22.47 | 28.72 | 25.00 | 26.37 | 25.00 | 34.00 | 24.9 | 4.8 | 19.3 |
| LGPCho 18:0p | 17.28 | 28.57 | 21.61 | 16.67 | 24.34 | 21.94 | 27.54 | 19.02 | 17.68 | 26.49 | 18.01 | 21.7 | 4.4 | 20.2 |
| GPCho 30:0a | 11.73 | 21.43 | 12.35 | 12.67 | 14.47 | 14.19 | 15.22 | 9.78 | 13.41 | 15.89 | 16.15 | 14.3 | 3.0 | 21.2 |
| GPCho 38:2a | 41.86 | 56.25 | 63.42 | 80.00 | 65.85 | 87.50 | 78.12 | 82.35 | 70.27 | 79.31 | 50.00 | 68.6 | 14.6 | 21.3 |
| GPCho 34:0e | 6.79 | 8.57 | 6.79 | 9.33 | 11.84 | 9.03 | 11.59 | 13.04 | 12.20 | 10.60 | 9.32 | 9.9 | 2.1 | 21.3 |
| GPCho 32:1p | 25.26 | 15.05 | 30.56 | 19.54 | 19.79 | 22.47 | 22.34 | 23.75 | 16.48 | 17.71 | 16.00 | 20.8 | 4.6 | 22.3 |
| GPIns 38:4 | 13.52 | 20.27 | 15.11 | 14.77 | 10.75 | 17.97 | 16.27 | 15.24 | 15.62 | 13.51 | 11.61 | 15.0 | 2.7 | 18.0 |
| GPIns 36:2 | 7.32 | 5.48 | 4.00 | 8.00 | 3.58 | 5.22 | 6.78 | 6.35 | 6.88 | 4.32 | 3.23 | 5.6 | 1.6 | 29.2 |

Lactate, Glucose and Creatinine

| Sample Name | QAlow C2 | QAlow C3 | QAlow C4 | QAlow C5 | QAlow C6 | QAlow C7 | QAlow C8 |
|---|---|---|---|---|---|---|---|
| Lactate | 21513.0 | 24282 | 25798 | 25443 | 22912 | 22519 | 23778 |
| Glucose | 3826 | 4250 | 4383 | 4104 | 4235 | 4288 | 4486 |
| Creatinine | 213.62 | 270.39 | 247.02 | 243.48 | 242.64 | 233.51 | 280.19 |

| Sample Name | QAlow C9 | QAlow C10 | QAlow C11 | QAlow C12 | mean [μmol/l] | std | CV [%] |
|---|---|---|---|---|---|---|---|
| Lactate | 21673 | 22400 | 24968 | 23625 | 23537 | 1473 | 6.3 |
| Glucose | 4156 | 3949 | 3983 | 3981 | 4149 | 202 | 4.9 |
| Creatinine | 263.16 | 262.74 | 238.50 | 244.91 | 249.1 | 18.7 | 7.5 |

Example 3

Therapeutic Drug Monitoring

Immunosuppressants are required to inhibit organ rejection after transplantation. The immunosuppressants used are Everolimus, Cyclosporin A, Tacrolimus, Sirolimus, and Mycophenolic acid. Therapeutic drug monitoring results prepared from a suitably prepared multi-device similarly as described above is shown here to further illustrate the use of the multi-device and support the claims of the invention.

Preparation and Conditions of Multi-Device

This multi-device was prepared with exactly the same method as described above, but instead using a single 8 mm cellulose spot (cut from generic card—10 539 859, Schlicher Schuell, Biosciences GmbH, Dassel, Germany) as the porous support.

Into the two multi-devices wells were placed a methanol solution (20 μl) containing Everolimus (200 ng/mL) (Sigma, Vienna, Austria), an internal standard for Sirolimus and Tacrolimus, and Cyclosporin D (400 ng/mL) (Sigma, Vienna, Austria), an internal standard for Cyclosporin A, was pipetted (Gilson 20 μl pipette) onto the porous supports of the multi-device and allowed to dry at room temperature for 30 minutes. Calibrator mixture and quality control levels I-V (whole blood calibrator set (level 0-6) for immunosuppressants, ClinChek R whole blood control for immunosuppressants, Recipe Chemicals and Instruments GmbH, Munich, Germany) were reconstituted according to manufactures instruction and both stored at −20° C. Prior to use, six calibrator solutions with increasing concentrations of Cyclosporin D and Everolimus and five quality control solution with various concentrations of Cyclosporin A, Tacrolimus, Sirolimus and Everolimus were thawed and allowed to reach room temperature around 23° C. Into six wells 20 µl of each six calibrators were pipetted (20 µl Gilson pipette) onto porous supports of multi-device. The five quality controls were pipetted into five separate wells porous supports of multi-device. To the multi-device was added acetonitrile (HPLC grade) immediately (Gilson 200 ml pipette) onto the multi-devices porous supports and instantly shaken with an orbital shaker at less than 600 rpm for 30 minutes. The eluant was collected by placing a 300 µl capacity microtitre capture plate under the device and then centriguation of the two at 500 g for 6 minutes. The eluant was then analyzed by mass spectrometric technique based on a published method (T. Koal, M. Deters, B. Casetta, V. Kaever, Simultaneous determination of four immunosuppressants by means of high speed and robust on-line solid phase extraction-high performance liquid chromatography-tandem mass spectrometry, J. Chromator. B, Analyt. Technol. Biomed. Life Sci. Jun. 15, 2004, 805(2); 215-222). A representative example of how the results are obtained and calculated are presented in FIG. 10 for Cyclosporin A analysis with LCMS to generate quantitative data. The areas under the integrated peaks of the internal standard Cyclosporin D were used for comparison against the area under the peak of the immunosuppressant Cyclosporin A in the five quality control samples containing known amounts.

FIGS. 11 to 14 show linear standard curves for all four immunosuppressants Cyclosporin A, Tacrolimus, Everolimus and Sirolimus using cellulose supports as inserts within the multi-device. Table 4 shows the calculated concentratons and the actual for accuracy comparisons of the five quality assurance materials analyzed.

tated pathways. Thereby the invention for the first time overcomes most of the bottlenecks in (pre)analytics, automatization and data processing and interpretation that have prohibited so far wide-spread quantitative metabolomics mining.

Compared to prior art analytical methods and devices, the quantitative analysis of the invention is extremely rugged and the results are highly reproducible. In particular, the metabolite data is much superior to comparable proteome or transcriptome data. Only about 10 µl blood or serum or about 20 µl urine or less than about 100,000 cultured cells are needed.

The performance features of the analytical method and the device can meet both research (discovery) application and subsequently clinical diagnostic standards. This ensures or makes possible quality assured data, standardized data, which is comparable from laboratory to laboratory, rapid turn-around time, "ready to go" implementation (hits), easily received data interpretation and visualization and a very high degree in automatization and standardization (SOPs). The overall costs/data point makes the metabolome information orders of magnitudes less expensive than proteome information.

The quantitative information obtained by the method or the device of the invention covers pathways and metabolites in a systemic (system biology) context and scalable fashion. Thereby, a representative functional picture or screen shot or metabolic fingerprint of intermediary metabolism can be finally derived from arrays of marker metabolites.

Moreover, functional end-point information that is annotated and can conveniently be linked to information sources of

TABLE 4

Industrial Applicability

| | | Analyte Concentration (ng/mL) | Calculated Concentration (ng/mL) | Accuracy (%) | | | Analyte Concentration (ng/mL) | Calculated Concentration (ng/mL) | Accuracy (%) |
|---|---|---|---|---|---|---|---|---|---|
| Cyc A | Calibrator 0 | 0.2 | 0.201 | 101 | Sirolimus | Calibrator 0 | 0 | No Peak | N/A |
| | Calibrator 1 | 46.7 | 43.8 | 93.7 | | Calibrator 1 | 2.4 | 2.81 | 117 |
| | Calibrator 2 | 115 | 116 | 101 | | Calibrator 2 | 6.6 | 6.38 | 96.7 |
| | Calibrator 3 | 304 | 315 | 103 | | Calibrator 3 | 12.7 | 12.8 | 101 |
| | Calibrator 4 | 483 | 472 | 97.7 | | Calibrator 4 | 19.6 | 19.6 | 99.8 |
| | Calibrator 5 | 777 | 820 | 106 | | Calibrator 5 | 29 | 31.5 | 109 |
| | Calibrator 6 | 1940 | 1900 | 97.9 | | Calibrator 6 | 49.4 | 46.7 | 94.4 |
| | QA1 | 61 | 45.3 | 74.2 | | QA1 | 3.04 | 2.46 | 80.8 |
| | QA2 | 116 | 95.5 | 82.3 | | QA2 | 8.65 | 10.1 | 117 |
| | QA3 | 254 | 220 | 86.7 | | QA3 | 15.3 | 12.6 | 82.4 |
| | QA4 | 474 | 391 | 82.6 | | QA4 | 0 | No Peak | N/A |
| | QA5 | 1340 | 1310 | 98.1 | | QA5 | 0 | No Peak | N/A |
| Tacrolimus | Calibrator 0 | 0.1 | No Peak | N/A | Everolimus | Calibrator 0 | 0 | <0 | N/A |
| | Calibrator 1 | 2.1 | 2.17 | 103 | | Calibrator 1 | 2.1 | 2.46 | 117 |
| | Calibrator 2 | 5.6 | 5.38 | 96 | | Calibrator 2 | 6 | 5.71 | 95.1 |
| | Calibrator 3 | 10.9 | 10.5 | 95.9 | | Calibrator 3 | 12.3 | 12.5 | 101 |
| | Calibrator 4 | 15.8 | 16.1 | 102 | | Calibrator 4 | 18.2 | 18.3 | 100 |
| | Calibrator 5 | 21.9 | 22 | 101 | | Calibrator 5 | 25.3 | 27.1 | 107 |
| | Calibrator 6 | 38.8 | 38.9 | 100 | | Calibrator 6 | 46.5 | 44.4 | 95.5 |
| | QA1 | 3.23 | 3.69 | 114 | | QA1 | 3.48 | 3.18 | 91.3 |
| | QA2 | 6.6 | 7.35 | 111 | | QA2 | 11.1 | 10.8 | 97.3 |
| | QA3 | 13.2 | 14.8 | 112 | | QA3 | 18.2 | 18.5 | 102 |
| | QA4 | 0 | 0.246 | N/A | | QA4 | 0 | No Peak | N/A |
| | QA5 | 0 | 0.355 | N/A | | QA5 | 0 | No Peak | N/A |

The invention makes possible a versatile and standardized analysis of various biofluids and tissues. For example, current in-house capacities can demonstrate simultaneous and fully automated sample preparation and analysis, generating more than 1000 quantitative and annotated data points from 10 µl of dried blood within 6 minutes of MS machine time covering various classes of metabolites within more than 100 annothe proteome, transcriptome and genome, recruiting metabolome information for system biology needs.

The device and the method can be used in an integrated tool (software and analytical) suitable to establish a new "standard" for simultaneous generation of large scale quantitative identified and annotated metabolite profiles and the study of complex and dynamic multiple biomaker patterns. Moreover, commercially available hardware components, consisting of a liquid handling system for automated and standardized sample preparation and a mass spectrometer for MS-MS analytics, can be integrated by proprietary and protected designed consumable-based products and application software, comprising (pre-) analytical procedures and innovative modules for quality controlled data processing, technical validation and documentation, statistical analysis and biochemical interpretation.

The sample preparation time in the invention (hit-based in batch of 90 samples/microtitre tray) is only roughly 2 h, and will be further reduced by means of parallelization through the scheduling software. A wide range of specific internal standards for quantification is pre-formulated in proprietary chemistry as integral part of usually one or two step reaction preparation and application hits, as is contained all necessary material for QC and QA in combination with software and SOPs.

Industrial applications include biomarker discovery and commercialization with the objective to utilize validated biomarkers for disease diagnosis, treatment efficacy or toxicity. The main applications in pharmaceutical development include the areas drug metabolism and pharmacokinetics, toxicology and safety, drug efficacy and pharmacodynamics. Other fields comprise clinical diagnostics and theranostics, where, for example, early, sensitive and specific diagnosis and accurate staging facilitates disease prevention instead of costly interventions and allows personalized treatment, and where therapeutic effects can be specifically monitored supporting personalized treatment. Further application areas include, but are not limited to, nutrition industry, wellness, homeland security, and basic biology.

It is to be understood that the foregoing descriptions and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

The invention claimed is:

1. An apparatus adapted to analyze a drug and/or metabolite profile in a biological sample containing at least one drug and/or metabolite, wherein the biological sample can be divided into aliquoted samples, the apparatus comprising:
    an input unit adapted to input at least one drug and/or metabolite to be screened;
    a controlling unit coupled to an input unit and connected to a database, the controlling unit being adapted to determine a parameter set for at least one drug and/or metabolite preparation and for mass spectrometry analyses depending on the input of the kind of the at least one drug and/or metabolite to be screened;
    a treatment unit adapted to prepare the at least one drug and/or metabolite to be screened depending on the at least one determined parameter set, the treatment unit comprising an automated liquid handling system, and at least one device adapted to derivatize the at least one drug and/or metabolite present in the sample and to subsequently extract the derivatives, the device comprising
    (A) one or more wells,
    (B) one or more inserts located in the wells, wherein the insert comprises a support comprising a sorbent material for liquids which support is impregnated with at least one organic internal standard; and
    (C) a retainer holding the insert within the well with a distance between the insert and the walls and the bottom of the well in order to allow a free circulation of fluids around the insert;
    a mass spectrometer adapted to perform mass spectrometry analyses on the at least one prepared drug and/or metabolite depending on the parameter set; and
    a database coupled to an evaluation unit, the database being adapted to store results of analyzing and parameter sets for drug and/or metabolite preparation and for mass spectrometry analyses; wherein the database is adapted to include updated information derived from comparing the results of the mass spectrometry with reference results stored in the database, wherein the results of mass spectrometry are evaluated by the evaluation unit utilizing reference results stored in the database to output an analysis of the drug and/or metabolite profile.

2. The apparatus as claimed in claim 1, wherein the at least one prepared drug and/or metabolite is supplied to the mass spectrometer after being extracted.

3. The apparatus as claimed in claim 1, including a processing unit for at least one of data filtration, concentration calculation, normalization, verification and annotation of mass spectrometric results.

4. A method for analysis of a drug and/or metabolite profile in a biological sample, comprising the steps of:
    providing the sample to an apparatus as defined in claim 1 for analyzing drugs and/or metabolites;
    optionally dividing the sample into aliquots of small samples;
    providing information of the drug and/or metabolite to be screened to the apparatus;
    determining a parameter set for drug and/or metabolite preparation and for mass spectrometry analyses depending on the information of the drug and/or metabolite to be screened;
    preparing the sample depending on the information of the drug and/or metabolite to be screened;
    extracting the prepared drugs and/or metabolites;
    providing the mass spectrometer with a sample extract;
    performing one or more mass spectrometry analyses on the prepared drugs and/or metabolites;
    evaluating and processing results of mass spectrometry of the drugs and/or metabolites to be screened and compare with reference values;
    generating output data, wherein the database is adapted to include updated information derived from comparing the results of the mass spectrometry with reference results stored in the database.

5. The method as claimed in claim 4, wherein the step of providing information of the drugs and/or metabolites to be screened further comprises:
    prompting for a checklist of at least one of a sample number, internal standard, consumable, solvent, SOP type, or LIMS style of tracking.

6. The method as claimed in claim 4, further comprising the steps of: combining the sample with at least one internal standard, consumable or solvent or a combination thereof; and
    treating the combined samples depending on a parameter set supplied to the apparatus; wherein the parameter set is supplied depending on the information of the drugs and/or metabolites to be screened.

7. The method as claimed in claim 4, wherein the step of preparing the drug and/or metabolite further comprises: derivatizing and/or extracting the prepared drugs and/or metabolites from aliquoted samples.

8. The apparatus as claimed in claim 1, wherein the treatment unit is adapted to combine the sample with at least one of any of internal standards, consumables, solvents or a combination thereof, wherein the combining is performed depending on the input of the kinds of drugs and/or metabolites to be screened.

9. The apparatus as claimed in claim 8, wherein the combined samples are treated according to the supplied parameter set in the treatment unit to provide a prepared drug and/or metabolite.

10. The apparatus as claimed in claim 1, wherein a plurality of samples are provided as multiple combinations to the treatment unit for being prepared by various methods/parameter sets with different internal standard, consumables or solvents to give multiple prepared extracts.

11. The method as claimed in claim 4, further comprising the steps of: dividing the sample into aliquots of small samples;
   combining each of the aliquoted samples with different internal standards, consumables or solvents;
   treating each of the aliquoted samples according to the parameter set;
   providing the prepared drug and/or metabolite extracts to the mass spectrometer and analyzing drugs and/or metabolites based on the parameter set;
   processing the mass spectrometer results comprising at least one of the steps: data filtration, concentration calculation, normalization, verification, linkage to pre-annotated biochemical and functional properties and storage of results and generated drug and/or metabolite concentration profile to a database; and
   after storing mass spectrometry results in the database, evaluating and comparing the results to reference results stored in the database.

12. The method as claimed in claim 11, wherein the step of evaluating and comparing the results to reference results stored in the database further comprises:
   statistical and chemometric analyzing of annotated drugs and/or metabolites;
   visualizing annotated drugs and/or metabolites onto pre-defined and new biochemical pathways; and
   discovering annotated drug and/or metabolite biomarker candidates for further evaluation and validation.

* * * * *